(12) United States Patent
Wu et al.

(10) Patent No.: US 9,821,162 B2
(45) Date of Patent: Nov. 21, 2017

(54) DEEP BRAIN STIMULATION FOR SLEEP DISORDERS

(71) Applicant: Medtronic, Inc., Minneapolis, MN (US)

(72) Inventors: Jianping Wu, Shoreview, MN (US); Rahul Gupta, Irvine, CA (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/685,690

(22) Filed: Apr. 14, 2015

(65) Prior Publication Data

US 2015/0306391 A1    Oct. 29, 2015

Related U.S. Application Data

(60) Provisional application No. 61/984,262, filed on Apr. 25, 2014.

(51) Int. Cl.
*A61N 1/36* (2006.01)
*A61B 5/00* (2006.01)
(Continued)

(52) U.S. Cl.
CPC ........ *A61N 1/36078* (2013.01); *A61B 5/4809* (2013.01); *A61B 5/4812* (2013.01);
(Continued)

(58) Field of Classification Search
CPC .................................................. A61N 1/36078
See application file for complete search history.

(56) References Cited

U.S. PATENT DOCUMENTS 7,277,758 B2    10/2007    DiLorenzo
7,491,181 B2    2/2009    Heruth et al.
(Continued)

FOREIGN PATENT DOCUMENTS

CN    102626538 A    8/2012

OTHER PUBLICATIONS

Vitek, M.D., Ph.D., et al., "External pallidal stimulation improves parkinsonian motor signs and modulates neuronal activity throughout the basal ganglia thalamic network," Exp Neurol., Jan. 2012, 11 pp.
(Continued)

*Primary Examiner* — Eric D. Bertram
(74) *Attorney, Agent, or Firm* — Shumaker & Sieffert, P.A.

(57) ABSTRACT

In some examples, a medical device delivers electrical stimulation to the external portion of the globus pallidus of a brain of a patient in order to treat a sleep impairment of the patient. In some examples, the electrical stimulation may be delivered via one or more electrodes implanted in the GPe of the brain. In some examples, an electrical stimulation device is configured to deliver electrical stimulation therapy to the GPe based on detection of a sleep state of a patient. The sleep state may include, for example, a state in which the patient is awake and intending on sleeping, is awake and attempting to sleep or has initiated sleep. In addition, in some examples, an electrical stimulation device is configured to deliver electrical stimulation therapy to the GPe based on detection of an awake state of a patient.

48 Claims, 5 Drawing Sheets

(51) Int. Cl.
*A61B 5/048* (2006.01)
*A61N 1/05* (2006.01)

(52) U.S. Cl.
CPC ........ *A61B 5/4836* (2013.01); *A61N 1/36139* (2013.01); *A61B 5/048* (2013.01); *A61N 1/0534* (2013.01); *A61N 1/36132* (2013.01); *A61N 1/36167* (2013.01)

(56) References Cited

U.S. PATENT DOCUMENTS

| | | | |
|---|---|---|---|
| 7,519,431 | B2 | 4/2009 | Goetz et al. |
| 7,769,464 | B2 | 8/2010 | Gerber et al. |
| 7,974,696 | B1 | 7/2011 | DiLorenzo |
| 8,055,348 | B2 | 11/2011 | Heruth et al. |
| 8,121,694 | B2 | 2/2012 | Molnar et al. |
| 8,290,596 | B2 | 10/2012 | Wei et al. |
| 8,364,272 | B2 | 1/2013 | Goetz |
| 2005/0065427 | A1 | 3/2005 | Magill et al. |
| 2005/0209512 | A1 | 9/2005 | Heruth et al. |
| 2005/0209644 | A1 | 9/2005 | Heruth et al. |
| 2008/0071326 | A1 | 3/2008 | Heruth et al. |
| 2009/0099627 | A1 | 4/2009 | Molnar et al. |
| 2009/0192556 | A1* | 7/2009 | Wu ............... A61B 5/0031 607/3 |
| 2009/0264789 | A1 | 10/2009 | Molnar et al. |
| 2011/0112590 | A1 | 5/2011 | Wu et al. |
| 2012/0271375 | A1 | 10/2012 | Wu et al. |
| 2014/0094823 | A1 | 4/2014 | Carcieri et al. |

OTHER PUBLICATIONS

International Search Report and Written Opinion from counterpart International Application No. PCT/US2015/025919, dated Jun. 18, 2015, 10 pp.

U.S. Appl. No. 60/999,096 by Molnar et al., entitled "Device Control Based on Prospective Movement," filed Oct. 16, 2007.

U.S. Appl. No. 60/999,097 by Denison et al., entitled "Responsive Therapy System," filed on Oct. 16, 2007.

Qiu et al., "Basal ganglia control of sleep—wake behavior and cortical activation," European Journal of Neuroscience, vol. 31, Feb. 2010, 16 pp.

International Preliminary Report on Patentability from International Application No. PCT/US2015/025919, mailed Nov. 3, 2016, 7 pp.

Schafer et al., "Effects of Parkinsonian Medication on Sleep," Journal of Neurology, vol. 247, Supplement 4, Sep. 2000, 5 pp.

Pal et al., "A study of excessive daytime sleepiness and its clinical significance in three groups of Parkinson's disease patients taking pramipexole, cabergoline and levodopa mono combination therapy," Journal of Neural Transmission, vol. 108, Issue 1, Jan. 2001, 8 pp.

Zhang et al., "Lesions in monkey globus pallidus externus exacerbate parkinsonian symptoms," Experimental Neurology, vol. 199, Elsevier, Feb. 17, 2006, 8 pp.

Kuoppamaki et al., "Parkinsonism following bilateral lesions of the globus pallidus: performance on a variety of motor tasks shows similarities with Parkinson's disease," Journal of Neurology, Neurosurgery and Psychiatry, May 2005, 9 pp.

Clarenbach, "Parkinson's disease and sleep," Journal of Neurology, vol. 247, Supplement 4, Sep. 2000, 5 pp.

Dimpfel, "Pharmacological Modulation of Dopaminergic Brain Activity and its Reflection in Spectral Frequencies of the Rat Electropharmacogram," Neuropsychobiology, available online Jan. 14, 2009, 11 pp.

Fuller et al., "Reassessment of the structural basis of the ascending arousal system," National Institutes of Health, Journal of Comparative Neurology, Apr. 1, 2011, 38 pp.

Kallweit et al., "Dopaminergic Treatment in Idiopathic Restless Legs Syndrome: Effects on Subjective Sleepiness," Clinical Neuropharmacology, vol. 33, No. 6, Nov./Dec. 2010, 3 pp.

Klawans et al., "A Pure Parkinsonian Syndrome Following Acute Carbon Monoxide Intoxication," Brief Communications and Clinical Notes, Archives Neurology, vol. 39, May 1982, 3 pp.

\* cited by examiner

DEEP BRAIN STIMULATION FOR SLEEP DISORDERS

This application claims the benefit of U.S. Provisional Application No. 61/984,262, which was filed on Apr. 25, 2014 and is entitled, "DEEP BRAIN STIMULATION FOR SLEEP DISORDERS, the entire content of which is incorporated herein by reference.

TECHNICAL FIELD

The disclosure relates to electrical stimulation therapy, and, more particularly, deep brain stimulation.

BACKGROUND

In some cases, an ailment or medical condition may affect the quality of a patient's sleep. For example, neurological disorders may cause a patient to have difficulty falling asleep, and may disturb the patient's sleep, e.g., cause the patient to wake frequently during the night and/or early in the morning.

SUMMARY

The disclosure describes devices, systems, and methods for delivering electrical stimulation therapy to the external portion of the globus pallidus (also referred to herein as the "GPe," or "globus pallidus externus," or "lateral globus pallidus") of a brain of a patient in order to treat a sleep impairment of the patient. In some examples, the electrical stimulation may be delivered via one or more electrodes implanted in the GPe of the brain. In addition, some examples, an electrical stimulation device is configured to deliver electrical stimulation therapy to the GPe during a sleep state of the patient. The sleep state may include, for example, a state in which the patient is awake and intending on sleeping, is awake and attempting to sleep, or has initiated sleep (and is, therefore, asleep). In these examples, the electrical stimulation therapy may be configured to help the patient fall asleep, maintain sleep or certain sleep stages, achieve certain sleep stages, or affect the timing of the sleep stages relative to each other, relative to the initiation of sleep, or relative to another relevant reference point.

In some examples disclosed herein, an electrical stimulation device is configured to deliver electrical stimulation therapy to the GPe during an awake state of the patient, which may include, for example, a state in which the patient is awake and is not intending on sleep or is not attempting to fall asleep. In these examples, the electrical stimulation therapy may be configured to help the patient stay awake and not fall asleep.

In some examples, an electrical stimulation device may be configured to deliver electrical stimulation to the GPe to help treat a sleep disorder, and deliver electrical stimulation to one or more other regions of the brain to help treat a sleep disorder, a movement disorder, or another disorder. The other regions of the brain may include, for example, the subthalamic nucleus ("STN"), the internal portion of the globus pallidus ("GPi"), or both the STN and GPi.

In some examples, an electrical stimulation device may be configured to deliver electrical stimulation to the GPe to help treat a sleep disorder, and deliver electrical stimulation to one or more other regions of the brain to help treat a sleep disorder, a movement disorder, or another disorder. The other regions of the brain may include, for example, the subthalamic nucleus ("STN"), the internal portion of the globus pallidus ("GPi"), or both the STN and GPi.

In one aspect, the disclosure is directed to a method comprising determining, by a processor, a patient is in a sleep state, and controlling, by the processor, an electrical stimulation generator to deliver deep brain electrical stimulation to an external portion of a globus pallidus of a brain of the patient based on the determination that the patient is in the sleep state.

In another aspect, the disclosure is directed to a system comprising an electrical stimulation generator, and a processor configured to determine a patient is in a sleep state and control the electrical stimulation generator to deliver deep brain electrical stimulation to an external portion of a globus pallidus of a brain of the patient based on the determination that the patient is in the sleep state.

In another aspect, the disclosure is directed to a system comprising means for generating electrical stimulation, means for determining a patient is in a sleep state, and means for controlling the means for generating electrical stimulation to deliver deep brain electrical stimulation to an external portion of a globus pallidus of a brain of the patient based on the determination that the patient is in the sleep state.

In another aspect, the disclosure is directed to a computer-readable storage medium comprising instructions. The instructions cause a programmable processor to determine a patient is in a sleep state, and, in response to determining the patient is in the sleep state, control an electrical stimulation generator to deliver deep brain electrical stimulation to an external portion of a globus pallidus of a brain of the patient based on the determination that the patient is in the sleep state.

In another aspect, the disclosure is directed to a method comprising determining, by a processor, a patient is in an awake state, and controlling, by the processor, an electrical stimulation generator to deliver deep brain electrical stimulation to an external portion of a globus pallidus of a brain of the patient based on the determination that the patient is in the awake state.

In another aspect, the disclosure is directed to a system comprising an electrical stimulation generator, and a processor configured to determine a patient is in an awake state and control the electrical stimulation generator to deliver deep brain electrical stimulation to an external portion of a globus pallidus of a brain of the patient based on the determination that the patient is in the awake state.

In another aspect, the disclosure is directed to a system comprising means for generating electrical stimulation, means for determining a patient is in an awake state, and means for controlling the means for generating electrical stimulation to deliver deep brain electrical stimulation to an external portion of a globus pallidus of a brain of the patient based on the determination that the patient is in the awake state.

In another aspect, the disclosure is directed to a computer-readable storage medium comprising instructions. The instructions cause a programmable processor to determine a patient is in an awake state, and, in response to determining the patient is in the awake state, control an electrical stimulation generator to deliver deep brain electrical stimulation to an external portion of a globus pallidus of a brain of the patient based on the determination that the patient is in the awake state.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of the disclosure are set forth in the accompanying drawings and the description below. Other features, objects, and advantages of the systems, methods, and devices in accordance with the disclosure will be apparent from the description and drawings, and from the claims.

DETAILED DESCRIPTION

Figure 1:
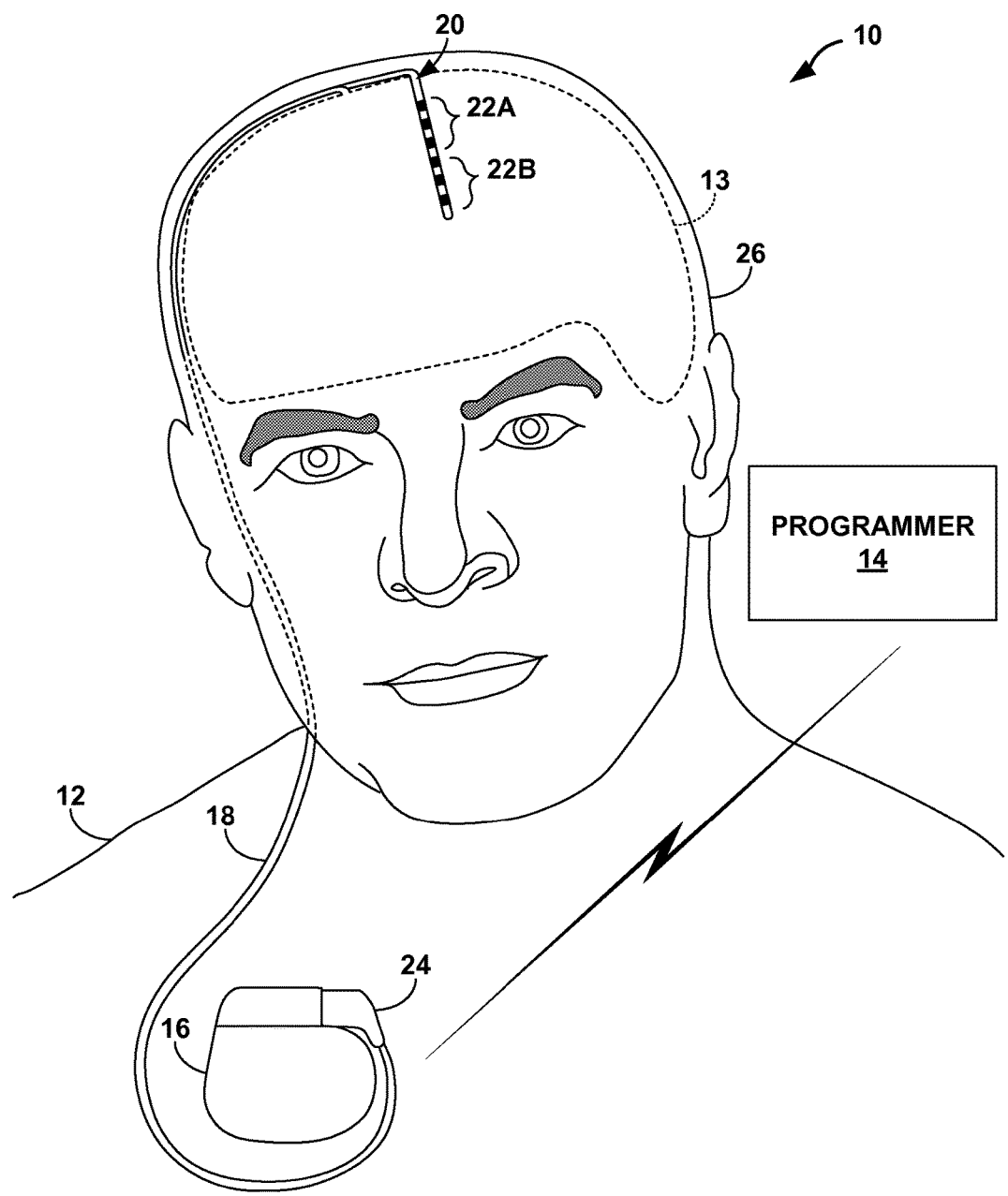
FIG. 1 is a conceptual diagram illustrating an example deep brain stimulation (DBS) system.

In examples described herein a medical device is configured to deliver electrical stimulation to the external portion of a globus pallidus ("GPe") of a brain of a patient in order to help manage symptoms of a sleep disorder of the patient. The medical device may deliver deep brain electrical stimulation to the GPe via one or more electrodes implanted in the GPe of the brain. In the examples described herein, the electrical stimulation may be delivered to a particular portion of the GPe, such as to a projection from the GPe to the prefrontal cortex. The sleep disorder may be caused by an ailment or medical condition and may include symptoms such as an impaired ability to fall asleep, an impaired ability to maintain sleep or certain sleep stages, or frequent transitions between being asleep and being awake. For example, some patients that are afflicted with neurological disorders may suffer from sleep disturbances, such as insomnia, disturbances in rapid eye movement (REM) sleep (e.g., REM sleep behavior disorders), disrupted sleep architecture, periodic limb movements or sleep respiratory disorders or daytime somnolence. Daytime somnolence may include excessive sleepiness caused by a decreased quality of sleep during the night resulting from an impaired ability to fall asleep or to stay asleep, or from an inability to maintain or achieve certain sleep stages. In some cases, treatments for neurological orders may themselves affect sleep quality.

Example neurological disorders that may negatively affect patient sleep quality include movement disorders, such as tremor, Parkinson's disease, multiple sclerosis, or spasticity. Uncontrolled movements associated with such movement disorders may cause a patient to have difficulty falling asleep, disturb the patient's sleep (e.g., may cause the patient to wake periodically), or cause the patient to have difficulty achieving deep sleep stages. Parkinson's disease may also cause REM (sleep) behavior disorders (RBD), in which case, a patient may act out dramatic and/or violent dreams, shout or make other noises (e.g., grunting) during the REM stage sleep. The sleep disorder symptoms may be related to nocturnal rigidity, hypokinesia, pain, effects of antiparkinsonian drugs, anxiety and depression (which may coexist with the movement disorder), and dysfunctions of one or more brain structures involved in sleep regulation. Further, in some cases, poor sleep quality may increase the frequency or intensity of symptoms experienced by the patient due to a neurological disorder. For example, poor sleep quality has been linked to increased movement disorder symptoms in movement disorder patients.

The delivery of electrical stimulation to the GPe of a brain of a patient may also be used to help improve sleep quality and time (or duration) of sleep caused by other patient conditions, which may or may not be neurological in origin. For example, delivery of electrical stimulation to the GPe of a brain of a patient may also be used to help improve sleep quality for patients with epilepsy or another seizure disorder, psychiatric (or psychological) disorders, chronic pain (whether neurological in origin or not), congestive heart failure, gastrointestinal disorders and incontinence.

Recent studies have shown that excitotoxic lesions of the GPe may reduce total sleep time and cause wakefulness (e.g., insomnia), while lesions in other basal ganglia structures, such as the subthalamic nucleus, the substantia nigra pars reticularta (SNr), or the internal portion of the globus pallidus do not show significant effects on sleep. In addition, experimental results indicate that deep brain electrical stimulation of the GPe may induce sleep in rat subjects. In the experiments, under anesthesia, six adult male rat subjects were implanted with recording electrodes (four electroencephalogram screws were placed into the skull and two electromyogram wires were placed under neck muscles), and a DBS twisted pair stimulation electrode was implanted in the GPe of the brains of the rat subjects. In a first session, the rat subjects received a sham electrical stimulation (via the implanted DBS electrodes) having an amplitude of about 1.0 microamp ($\mu A$) and a frequency of about 180 Hz, or electrical stimulation (via the implanted DBS electrodes) having an amplitude of above 100 $\mu A$ and a frequency of about 180 Hz for about two hours. The EEG and EMG were monitored during the electrical stimulation of the GPe. In a second session, electrical stimulation having an amplitude of about 100 uA and a frequency of about 180 Hz was delivered to the GPes of two rate subjects. The EEG and EMG were monitored during the electrical stimulation.

The sleep latency was examined in the rat subjects stimulated using the 100 $\mu A$ electrical stimulation compared to 1.0 $\mu A$ electrical stimulation using the Student's paired t-test ($p<0.01$). It was found that compared to the electrical stimulation of the GPe using the 1 $\mu A$ electrical stimulation, the electrical stimulation of the GPe stimulation at 100 uA was associated with significantly reduced sleep latency (controls: 88.8±19.6 (standard error (SE)) min. vs. DBS: 41.8±11.9 min., $p<0.01$, N=6 and 6/group respectively). Prior to receiving electrical stimulation, all of the rat subjects showed similar sleep behavior, and took in average of 88 minute to assume a sleep posture and maintained the sleep posture for at least 10 minutes. The rats that received the GPe electrical stimulation having an amplitude of about 100 uA and a frequency of about 180 Hz in only took 41 minutes to reach sleep onset. The time difference was statistically significant (88.8±19.6 (SE) min vs 41.8±11.9 min, p<0.01). Thus, the experimental results indicate that DBS of the GPe (e.g., relatively high-frequency electrical stimulation) may trigger sleep and help reduce sleep latency.

During the experimental results, it was found that electrical stimulation of the GPe (delivered to the GPe) at an amplitude higher than about 100 uA or a frequency higher than about 180 Hz triggers a dystonic behavior (especially in the upper body) towards the ipsilateral direction, while electrical stimulation of the GPe (delivered to the GPe) at an amplitude less than 100 uA and a frequency less than about 180 Hz has much fewer sleep effects.

The experimental results indicate that the GPe may be at least one of the components of the basal ganglia affecting sleep-wake behavior, and that the neural circuitry of the GPe may be involved in sleep promotion. For example, the GPe may be a structure of the brain that helps mediate dopamine control of motor and non-motor behaviors in the basal ganglia. In addition, these results indicate that the underlying neural pathway for sleep control in the brain may not include the internal portion of the globus pallidus or the substantia nigra pars reticularta, or their projection to the thalamus. Thus, modulating the electrical activity of the GPe (e.g., the projection from the GPe to the prefrontal cortex), such as with electrical stimulation, may be a direct neural mechanism by which sleep of the patient may be affected.

A certain level of electrical activity in the GPe may promote sleep and a different level of electrical activity may promote wakefulness. It is believed that electrical stimulation of the GPe may help promote sleep and, therefore, help reduce sleep latency. Sleep latency may refer to the time it takes a patient to fall asleep. In addition, electrical stimulation of the GPe may help induce development of sleep stages, which may improve the quality of the patient's sleep.

In some examples, a medical device comprises an electrical stimulation generator ("stimulation generator") configured to generate and deliver electrical stimulation to a patient and a processor configured to control the stimulation generator to deliver electrical stimulation to the GPe during a sleep state of the patient. The sleep state may include, for example, a state in which the patient is awake and intending on sleeping, is state in which the patient is awake and is attempting to sleep, or a state in which the patient has initiated sleep. Some patients may have difficulty falling asleep, and, therefore, delivering electrical stimulation to the GPe while the patient is awake and intending on sleep or attempting to sleep may provide therapeutic benefits to the patient. In addition, delivering electrical stimulation to the GPe while the patient is asleep may help the patient maintain sleep, achieve or maintain specific sleep stages, or affect the timing of the sleep stages relative to each other, relative to the initiation of sleep, or another relevant reference point.

In some examples, the processor is configured to control the stimulation generator to initiate delivery of electrical stimulation to the GPe of the patient in response to detecting a sleep state of the patient. The processor may control the stimulation generator to deliver the electrical stimulation to the GPe substantially continuously (e.g., continuously or nearly continuously) or periodically during the sleep state (e.g., according to a predetermined schedule or cycle) and terminate the delivery of the electrical stimulation to the GPe in response to detecting an end of the sleep state (e.g., in response to detecting the awake state).

In addition, in some examples, the processor may control the stimulation generator to deliver the electrical stimulation to the GPe based on a determined sleep stage of the patient. The processor may determine the sleep stage based on a biosignal that is indicative of activity within the brain of the patient. Examples of biosignals indicative of activity within a brain of a patient include, but are not limited to, bioelectrical brain signals, such as electrical signals generated from local field potentials (LFPs) within one or more regions of the brain, such as, but not limited to, an electroencephalogram (EEG) signal or an electrocorticogram (ECoG) signal. In some examples, the electrical signals within the brain of the patient may reflect changes in electrical current produced by the sum of electrical potential differences across brain tissue.

Controlling the stimulation generator may include activating electrical stimulation, deactivating electrical stimulation, increasing an intensity of electrical stimulation, or decreasing an intensity of electrical stimulation based on the determined sleep stage. Intensity of stimulation may be a function of, for example, any one or more of the voltage or current amplitude value of the stimulation signal, frequency of stimulation signals, signal duration (e.g., pulse width in the case of stimulation pulses), signal burst pattern, and the like. In the case of pulses, frequency also may be referred to as pulse rate. The intensity of stimulation may, for example, affect the volume of tissue that is activated by the electrical stimulation.

The delivery of electrical stimulation to the GPe may be used as a stand-alone therapy, or may be used in conjunction with one or more other electrical stimulation therapies, drug delivery therapies, or other therapies. For example, a medical device that is configured to deliver electrical stimulation to the GPe may also be configured to deliver electrical stimulation to one or more other portions of the brain to further treat the sleep disorder or to treat another disorder. For example, the medical device may be configured to deliver electrical stimulation to the STN, the GPi, or both to help manage symptoms of a movement disorder of the patient. The sleep disorder for which the electrical stimulation therapy to the GPe is used to treat may or may not be related to the movement disorder. Electrical stimulation of the GPe of the brain of the patient may more directly target symptoms associated with a sleep disorder of the patient than electrical stimulation of the STN or the GPi.

In accordance with some example techniques, therapy delivery to the GPe and at least one of the STN or the GPi may be independently controlled, such that stimulation delivered to the GPe may occur at a different time and based on different control parameters (e.g., different sleep stages or brain signals) than therapy delivery to the at least one of the STN or the GPi. As a result, in some cases, stimulation is delivered to the GPe and not the STN or the GPi, while in other cases, stimulation is delivered to at least one of the STN or the GPi and not the GPe. In addition, in some cases, stimulation is delivered to both the GPe and at least one of the STN and the GPi. The electrical stimulation parameters with which the medical device generates and delivers electrical stimulation to the GPe can be the same or different as the electrical stimulation parameters with which the medical device generates and delivers electrical stimulation to the STN or GPi. In this way, the target tissue site or stimulation therapy can be selected to better address patient symptoms, some of which may be observed during one sleep stage, but not another sleep stage.

In some examples, electrical stimulation may be delivered to the GPe of a patient according to a first therapy program and to at least one of the STN or the GPi of the patient according to a second therapy program that defines at least one stimulation parameter that is different than the first therapy program. Electrical stimulation therapy according to the first and second therapy programs may be delivered independently, simultaneously, and/or alternatively. In some examples, the first and second therapy programs may be selected or modified based on the determined sleep stage of the patient or the first and second therapy programs may be modified based on the determined sleep stage.

In some examples, the processor may control the stimulation generator to deliver electrical stimulation to the GPe and the STN, or the GPe and the GPi, or the GPe and both the STN and the GPi via different implantable electrodes of a single implantable lead of the electrical stimulation device or via different implantable electrodes of two or more implantable leads, where the electrodes are positioned to independently stimulate the GPe and the at least one of the STN and GPi. That is, the different electrodes of the one or more leads can be arranged to deliver stimulation to only one of the GPe, STN, and GPi at a time, or, if desired, two or more of the GPe, STN, and GPi.

FIG. 1 is a conceptual diagram illustrating an example deep brain stimulation (DBS) system 10 that is configured to deliver electrical stimulation to a GPe of brain 13 of patient 12 to treat a sleep disorder of patient 12. DBS system 10 includes medical device programmer 14, implantable medical device (IMD) 16, lead extension 18, and lead 20 with electrodes 22A and 22B (collectively referred to as "electrodes 22"). IMD 16 includes a therapy module that includes a stimulation generator that is configured to generate and deliver electrical stimulation therapy to patient 12 via electrodes 22 of lead 20, as well as a processor that controls delivery of electrical stimulation to brain 13. Patient 12 ordinarily will be a human patient. In some cases, however, DBS system 10 may be applied to other mammalian or non-mammalian non-human patients.

IMD 16 is constructed of a biocompatible material that resists corrosion and degradation from bodily fluids. IMD 16 may comprise a hermetic housing or a near hermetic housing to substantially enclose components, such as a processor, a therapy module, and a memory. IMD 16 may be implanted within a subcutaneous pocket above the clavicle, on or within cranium 26, within the patient's back, abdomen, or buttocks of patient, or at any other suitable place within patient 12. Implanted lead extension 18 is coupled to IMD 16 via connector 24 (also referred to as a header of IMD 16). In the example of FIG. 1, lead extension 18 traverses from the implant site of IMD 16 and along the neck of patient 12 to cranium 26 of patient 12 to access brain 13. In the example shown in FIG. 1, lead 20 is implanted within brain 13 of patient 12 in order to deliver electrical stimulation to one or more regions of brain 13. Other lead 20 and IMD 16 implant sites and configurations are contemplated. For example, IMD 16 may be implanted on or within cranium 26. Furthermore, DBS system 10 may comprise more than one implantable lead and more than one set of implantable electrodes. External programmer 14 wirelessly communicates with IMD 16 as needed to provide or retrieve therapy information.

Lead 20 may be implanted to position electrodes 22 at desired locations of brain 13 through a hole in cranium 26. Lead 20 may be placed at any location within brain 13 such that electrodes 22 are capable of providing electrical stimulation to target tissue sites within brain 13 during treatment. For example, in examples, electrodes 22 may be surgically implanted under the dura mater of brain 13 or within the cerebral cortex of brain 13 via a burr hole in cranium 26 of patient 12, and electrically coupled to IMD 16 via one or more leads 20.

In the example shown in FIG. 1, electrodes 22 of lead 20 are shown as ring electrodes. Ring electrodes may be used in DBS applications because they are relatively simple to program and are capable of delivering an electrical field to any tissue adjacent to electrodes 22. In other examples, electrodes 22 may have different configurations. For example, in some examples, electrodes 22 of lead 20 may have a complex electrode array geometry that is capable of producing shaped electrical fields. The complex electrode array geometry may include multiple electrodes (e.g., partial ring or segmented electrodes) around the outer perimeter of lead 20, rather than one ring electrode. In this manner, electrical stimulation may be directed to a specific direction from lead 20 to enhance therapy efficacy and reduce possible adverse side effects from stimulating a large volume of tissue. In some examples, a housing of IMD 16 may include one or more stimulation and/or sensing electrodes. In alternative examples, lead 20 may have a shape other than an elongated cylinder as shown in FIG. 1. For example, lead 20 may be a paddle lead, a spherical lead, a bendable lead, or any other type of shape effective in treating patient 12.

IMD 16 is configured to deliver electrical stimulation therapy to the GPe of brain 13 of patient 12 to manage patient symptoms associated with the sleep impairment of patient 12, which, in some cases, is associated with a neurological disorder of patient 12, such as a movement disorder. In the example shown in FIG. 1, DBS system 10 includes a processor that determines whether patient 12 is in a sleep state, and controls delivery of electrical stimulation to the GPe of brain 13 of patient 12 during the sleep state, e.g., substantially continuously throughout the sleep state, or periodically during the sleep state. Thus, lead 20 may be positioned to deliver electrical stimulation to the GPe of brain 13 via one or more electrodes 22. The electrical stimulation delivered to the GPe may be configured to help decrease the sleep latency of patient 12.

In some examples, the processor may also be configured to determine a sleep stage of the sleep state based on a biosignal detected within brain 13 of patient 12, and may control delivery of electrical stimulation to the GPe based on a determined sleep stage. For example, a processor of DBS system 10 (e.g., a processor of programmer 14 or IMD 16) may control IMD 16 to activate electrical stimulation of the GPe, deactivate electrical stimulation delivered of the GPe, increase the intensity of electrical stimulation delivered to the GPe, or decrease the intensity of electrical stimulation delivered to the GPe (while still delivering some electrical stimulation to the GPe) based on the determined sleep stage.

Within a sleep state, patient 12 may be within one of a plurality of sleep stages. Example sleep stages include Stage 1 (also referred to as Stage N1 or S1), Stage 2 (also referred to as Stage N2 or S2), Deep Sleep (also referred to as slow wave sleep), and rapid eye movement (REM). The Deep Sleep sleep stage may include multiple sleep stages, such as Stage N3 (also referred to as Stage S3) and Stage N4 (also referred to as Stage S4). In some cases, patient 12 may cycle through the Stage 1, Stage 2, Deep Sleep, and REM sleep stages more than once during a sleep state. The Stage 1, Stage 2, and Deep Sleep sleep stages may be considered non-REM (NREM) sleep stages.

During the Stage 1 sleep stage, patient 12 may be in the beginning stages of sleep, and may begin to lose conscious awareness of the external environment. During the Stage 2 and Deep Sleep sleep stages, muscular activity of patient 12 may decrease, and conscious awareness of the external environment may disappear. During the REM sleep stage, patient 12 may exhibit relatively increased heart rate and respiration compared to the Stage 1, Stage 2, and Deep Sleep sleep stages. In some cases, the Stage 1, Stage 2, and Deep Sleep sleep stages may each last about five minutes to about fifteen minutes, although the actual time ranges may vary between patients. In some cases, REM sleep may begin about ninety minutes after the onset of sleep, and may last about five minutes to about fifteen minutes or more, although the actual time ranges may vary between patients.

The delivery of electrical stimulation to the GPe during a sleep state may be used as a standalone therapy, or may be used in conjunction with one or more other electrical stimulation therapies, drug delivery therapies, or other therapies. For example, IMD 16 may be configured to deliver electrical stimulation one or more other portions of the brain to further treat the sleep disorder or to treat another patient condition, such as, but not limited to, a movement disorder. In addition to electrical stimulation therapy, IMD 16 or another medical device may be configured to deliver a suitable pharmaceutical agent, such as acetylcholine, dopamine, epinephrine, norepinephrine, serotonine, inhibitors of noradrenaline or any agent for affecting a sleep disorder or combinations thereof to patient 12 (e.g., delivered to brain 13 or another region within patient 12).

In some examples, IMD 16 is also configured to deliver electrical stimulation therapy to one or more regions of brain 13 in addition to the GPe. For example, IMD 16 may be configured to deliver electrical stimulation therapy to the STN, GPi, or both the STN and GPi of brain 13. The GPe of brain 13 may play a role in sleep regulation and the STN and GPi of brain 13 may play a role in movement control. Delivery of electrical stimulation to at least one of the STN or the GPi may be an effective treatment for some movement disorders, such as Parkinson's disease, and the treatment for the movement disorder may also improve sleep quality in certain aspects, e.g., by decreasing sleep fragmentation. Patient 12 may also have a sleep disorder that may or may not be related to the movement disorder. While the DBS provided to manage symptoms of the patient's movement disorder may help improve sleep quality, other aspects of the sleep disorder may remain unimproved by the DBS to treat movement disorders. The delivery of electrical stimulation to the GPe of brain 13 by IMD 16 may help address these other aspects of the patient's sleep disorder, such as, but not limited to, reducing sleep latency. By reducing the sleep latency, patient 12 may feel more rested, and, as a result, DBS system 10 may help improve the quality of the patient's life.

Because the GPe is located relatively close (anatomically) to the STN and the GPi, lead 20 can be positioned in a manner that allows IMD 16 to deliver electrical stimulation therapy to the GPe and at least one of the STN or the GPi via a common lead 20. The distal (deepest) electrodes 22B, located in STN or GPi, can be used to deliver electrical stimulation that may improve motor symptoms of the patient and the proximal (shallower) electrodes 22A can be used to deliver electrical stimulation to the GPe to improve sleep of the patient (e.g., by regulating sleep) as necessary. Thus, in some examples, IMD 16 delivers electrical stimulation to at least one of the STN or the GPi via electrodes 22B in order to treat sleep disorder symptoms associated with movement control and delivers electrical stimulation to the GPe via electrodes 22A in order to effectively treat sleep disorder symptoms associated with sleep regulation. In some examples, sets of electrodes 22A, 22B share at least one electrode, while in other examples, sets of electrodes 22A, 22B do not have any common electrodes and are comprised of separate sets of electrodes. In other examples, however, IMD 16 may deliver electrical stimulation to the GPe and at least one of the STN or the GPi via separate leads or via more than one common lead.

Patients with Parkinson's disease or other neurological disorders may have a poor quality of sleep associated with difficulty regulating sleep. Delivery of electrical stimulation to one or more regions of brain 13 may be an effective treatment for sleep disorder symptoms associated with sleep regulation. For example, the GPe of brain 13 may play a role in regulating the sleep-wake cycle of patient 12; thus, delivery of electrical stimulation to the GPe of brain 13 during the entire sleep state or during a particular sleep stage may improve regulation of the sleep-wake cycle of patient 12.

In addition, patients with Parkinson's disease or other neurological disorders may have a poor quality of sleep or disruption of sleep timing associated with difficulty moving (e.g., akinesia, bradykinesia, or rigidity) during the sleep state in general or during a particular sleep stage. For example, an inability to move during the Stage 1 sleep stage, when patient 12 is attempting to initiate sleep, may be discomforting to patient 12, which may affect the ability of patient 12 to fall asleep. Delivery of electrical stimulation to one or more regions of brain 13 may be an effective treatment for sleep disorder symptoms associated with or caused by the movement disorder. For example, electrical stimulation of the STN and/or GPi of brain 13 during a particular sleep stage may increase the ability of patient 12 to initiate, maintain, or control movement naturally associated with or otherwise occurring during a particular sleep stage.

For example, during a sleep stage associated with the Stage 1 sleep stage, delivery of electrical stimulation to the STN via electrodes may improve the motor skills of patient 12, such that patient 12 may initiate movement or maintain movement, e.g., to adjust a sleeping position. As another example, patient 12 may become more physically active during the REM sleep stage. Patient 12 may involuntarily move his legs during the REM sleep stage or have other periodic limb movements. The physical activity of patient 12 may be disruptive to the patient's sleep, as well as to others around patient 12 when patient 12 is in the REM sleep stage. Accordingly, upon detecting a sleep stage associated with the REM sleep stage, delivery of electrical stimulation to the STN via electrodes may minimize the movement of patient 12 or allow patient 12 to control movement. However, in other examples, withholding the delivery of stimulation to the STN during the REM sleep stage may also help minimize patient movement during the REM sleep stage, which may help increase the quality of the patient's sleep.

In some examples, IMD 16 does not deliver stimulation to the STN during the Stage 2 and/or Deep Sleep sleep stages of patient 12. In other examples, IMD 16 delivers stimulation to the STN during the Stage 2 and/or Deep Sleep sleep stages of patient 12, but with a lower intensity relative to the stimulation delivered to the STN during the Stage 1 and REM sleep stages. The lower intensity may be defined by a threshold voltage amplitude, a threshold current amplitude, a threshold frequency, a threshold pulse width or another threshold signal characteristic.

Patients with movement disorders associated with a difficulty moving may find it difficult to get out of bed after waking up. Accordingly, in some examples, in response to determining that patient 12 is no longer in a sleep state (e.g., no longer asleep or attempting to sleep) based on biosignals sensed within brain 13, DBS system 10 may control delivery of electrical stimulation to help patient 12 undergo the physical movements involved in getting out of bed or to otherwise initiate movement. In contrast, therapy systems that only rely on motion detectors (e.g., accelerometers) to control therapy delivery may be ineffective for patients with Parkinson's disease or other difficulty initiating movement, because the patient may be awake but unable to move. In other words, a therapy system that relies primarily on an accelerometer or other motion sensors may be unable to determine when a Parkinson's patient has woken up because the patient may be unable to move. In contrast, DBS system 10 may select a therapy program that helps improve the motor skills of patient 12 upon detecting the patient's awake state (i.e., detecting that patient 12 is not sleeping), such that patient 12 may initiate movement or maintain movement, e.g., to help patient 12 get out of bed.

In some cases, different target tissue sites within brain 13 can provide efficacious therapy for different sleep stages of patient 12. In addition, different electrical stimulation parameter values for the therapy delivery to different regions of brain 13 may provide efficacious therapy (e.g., improved sleep quality) for different sleep stages of patient 12. Thus, in some examples, in which IMD 16 delivers electrical stimulation to the GPe and at least one other structure of brain 13, a processor of system 10 (e.g., of IMD 16 or programmer 14) may be configured to select a target tissue site within brain 13 for the electrical stimulation, electrical stimulation parameter values, or both, based on a current sleep stage of patient 12. The current sleep stage may be the sleep stage of patient 12 at approximately the same time (e.g., the same time or nearly at the same time) at which the sleep stage is determined. In these examples, rather than delivering electrical stimulation to at least one of the GPe, the STN or the GPi regardless of the patient's current sleep stage, DBS system 10 selectively controls delivery of electrical stimulation to at least one of the GPe, the STN or the GPi in order to provide efficacious therapy during a current sleep stage of patient 12. Dynamically changing the electrical stimulation parameter values based on the patient's sleep stage may be useful for addressing the patient's sleep disorder symptoms in a more efficient and symptom-specific manner. Example techniques for determining a sleep stage of patient 12 are described below with respect to FIG. 6.

DBS system 10 may store a plurality of therapy programs (e.g., a set of electrical stimulation parameter values), and at least one stored therapy program may be associated with at least one sleep stage and/or a target tissue site (e.g., the GPe, the STN, or the GPi). In some examples, a processor of IMD 16 or programmer 14 may select a stored therapy program that defines electrical stimulation parameter values for delivery of electrical stimulation to patient 12 based on a determined sleep stage and, in some cases, based on a selected target tissue site. In this way, the processor may control delivery of electrical stimulation to patient 12 based on the determined sleep stage. In some examples, at least one of the stored therapy programs is associated with a respective one of at least two different sleep stages. In addition, in some examples, at least one of the stored therapy programs is associated with at least two different sleep stages.

In other examples, DBS system 10 may modify at least one electrical stimulation parameter value of a stored therapy program (e.g., a set of therapy parameter values) based on a determined sleep stage. The modifications to the therapy program may be made based on stored instructions that are associated with the determined sleep stage. The modifications to the therapy program may include modifications that activate electrical stimulation to one or more target tissue sites, deactivate electrical stimulation, increase an intensity of electrical stimulation, or decrease an intensity of electrical stimulation based on the determined sleep stage.

In some examples, the stimulation generator of IMD 16 is configured to generate and deliver electrical pulses to patient 12. However, in other examples, the stimulation generator of IMD 16 may be configured to generate a continuous wave signal, e.g., a sine wave or triangle wave. IMD 16 may generate electrical stimulation therapy according to a therapy program that is selected at that given time in therapy, where the therapy program defines values for a set of therapy parameters. For example, in examples in which IMD 16 delivers electrical stimulation in the form of stimulation pulses, a therapy program may include a set of therapy parameter values, such as an electrode combination for delivering stimulation to patient 12, pulse frequency, pulse width, and a current or voltage amplitude of the pulses. The electrode combination may indicate the specific electrodes 22 (e.g., a subset of electrodes 22) that are selected to deliver stimulation signals to brain 13 of patient 12, and also the respective polarity of the selected electrodes.

Electrical stimulation of the GPe and the at least one of the STN or the GPi can have different physiological effects on patient 12. Thus, in some examples in which system 10 delivers electrical stimulation to the GPe and at least one of the STN or the GPi, a processor of system 10 is configured to independently control the delivery of electrical stimulation to the GPe and to the at least one of the STN or the GPi. To facilitate the independent control of electrical stimulation to the GPe and the at least one of the STN and the GPi, the sets of electrodes 22A and 22B can positioned to independently stimulate the GPe and the at least one of the STN or GPi. That is, IMD 16 can independently select the set of electrodes 22A (and not electrodes 22B) to deliver stimulation to the GPe or independently select the set of electrodes 22B (and not electrodes 22A) to deliver stimulation to the at least one of the STN or GPi. The independently selectable electrodes 22A, 22B that are positioned to deliver stimulation to respective target tissue sites provides IMD 16 with a plurality of configurations with which stimulation therapy can be delivered to patient 12.

IMD 16 can also be configured to manage another patient condition in addition to a sleep disorder. For example, delivery of electrical stimulation the STN or the GPi, or both, may also effectively treat symptoms associated with a movement disorder of patient 12 while patient 12 is in either of a sleep state or an awake state. Example techniques for delivering therapy to manage a movement disorder are described in U.S. Pat. No. 8,121,694 to Molnar et al., entitled "THERAPY CONTROL BASED ON A PATIENT MOVEMENT STATE," which issued on Feb. 21, 2012, U.S. Provisional Patent Application No. 60/999,096 by Molnar et al., entitled "DEVICE CONTROL BASED ON PROSPECTIVE MOVEMENT," which was filed on Oct. 16, 2007, and U.S. Provisional Patent Application No. 60/999,097 by Denison et al., entitled "RESPONSIVE THERAPY SYSTEM," which was filed on Oct. 16, 2007. The entire contents of the above-identified U.S. Pat. No. 8,121,694 and U.S. Provisional Patent Application Nos. 60/999,096 and 60/999,097 are incorporated herein by reference.

In some examples described by U.S. Pat. No. 8,121,694 and U.S. Provisional Patent Application Ser. No. 60/999,097, biosignals within brain 13, such as an EEG or ECoG signal, may be used to determine whether a patient is in a movement state or a rest state. The movement state includes the state in which the patient is generating thoughts of movement (i.e., is intending to move), attempting to initiate movement, or is moving. The rest state, in which patient 12 is not generating thoughts of movement (i.e., is intending to move), attempting to initiate movement, or is moving, can be used to detect a sleep state of patient 12 in some examples. The movement state or rest state determination may then be used to control therapy delivery. For example, in response to detecting a movement state of the patient, IMD 16 can deliver stimulation therapy to the STN of brain 13 of patient 12 in order to help manage movement disorder symptoms of patient 12. IMD 16 can deliver therapy to brain 13 (e.g., the STN) in order to help the patient initiate movement or maintain movement, and, upon detecting a rest state of the patient, therapy delivery may be deactivated or otherwise modified.

In the example shown in FIG. 1, IMD 16 includes a memory that stores a plurality of therapy programs that each defines a set of electrical stimulation parameter values. In some examples, in response to determining patient 12 is in a sleep state, IMD 16 may select a therapy program from the memory, where the therapy program is associated with the sleep state, and generate the electrical stimulation therapy to help manage the sleep impairment of patient 12 using the selected therapy program and deliver the electrical stimulation to the GPe via select electrodes 22. IMD 16 may, in some examples, deliver the electrical stimulation to the GPe substantially continuously throughout the sleep state, or periodically through the sleep state.

In some examples, in response to determining a current sleep stage or timing of these stages in relation to sleep posture or attempts to sleep of patient 12, e.g., by monitoring biosignals within brain 13, IMD 16 may select a therapy program from the memory, where the therapy program is associated with the current sleep stage, and generate the electrical stimulation to manage the patient symptoms associated with the determined sleep stage using the selected therapy program. If DBS system 10 is configured to provide therapy during a plurality of patient sleep stages, each sleep stage may be associated with a different therapy program in the memory of IMD 16, programmer 14, or another device because different therapy programs may provide more effective therapy for a certain sleep stage compared to other therapy programs. Alternatively, two or more sleep stages may be associated with a common therapy program. Accordingly, IMD 16 may store a plurality of therapy programs or programmer 14 may store a plurality of therapy programs that are provided to IMD 16 via wireless telemetry.

During a trial stage in which IMD 16 is evaluated to determine whether IMD 16 provides efficacious therapy to patient 12, a plurality of therapy programs may be tested and evaluated for efficacy relative to the sleep state or to one or more sleep stages. For example, a clinician may observe patient 12 during the sleep state and modify therapy delivery to patient 12 during each of the plurality of sleep stages in order to determine which therapy programs (e.g., sets of therapy parameter values) provide efficacious therapy to patient 12 during the respective sleep stage. In some examples, patient 12 can provide feedback (when in the awake state) as to the quality of the sleep state, which can indicate whether the trial therapy programs selected for delivery during the sleep state or particular sleep stages were efficacious. While a clinician can (but need not) rely on a known set of parameter values to initiate the trial therapy delivery, different therapy parameter values may provide efficacious therapy for different patients. Therapy programs may be selected for storage within IMD 16 based on the results of the trial stage. Therefore, the trial stage may be useful for customizing the therapy parameter values stored and implemented by IMD 16 for a particular patient 12.

During chronic therapy in which IMD 16 is implanted within patient 12 for delivery of electrical stimulation on a non-temporary basis, one or more therapy programs may be used to deliver electrical stimulation therapy to the GPe of brain 13 of patient 12 during a sleep state. In addition, in some examples, different therapy programs may be used to deliver electrical stimulation therapy to the GPe, where the therapy program may be selected based on a determined sleep stage of patient 12. In some cases, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust electrical stimulation parameters, switch between programs, or undertake other therapy adjustments. Patient 12 may generate additional programs for use by IMD 16 via external programmer 14 at any time during therapy delivery or as designated by the clinician.

Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. The clinician may also store therapy programs within IMD 16 with the aid of programmer 14. During a programming session, the clinician may determine one or more therapy programs that may provide efficacious therapy to patient 12 to address symptoms associated with the sleep state or with one or more specific sleep stages of the sleep state. Programmer 14 may be used to control delivery of electrical stimulation by IMD 16, such as by activating electrical stimulation, deactivating electrical stimulation, increasing an intensity of electrical stimulation, or decreasing an intensity of electrical stimulation based on a sleep stage of patient 12.

When programmer 14 is configured for use by the clinician, programmer 14 may be used to transmit initial programming information to IMD 16. This initial information may include hardware information, such as the type of lead 20 and the electrode 22 arrangement, the position of lead 20 within brain 13, the configuration of electrode array 22, initial programs defining electrical stimulation parameter values, and any other information the clinician desires to program into IMD 16. Programmer 14 may also be capable of completing functional tests (e.g., measuring the impedance of electrodes 22).

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device may run an application that enables the computing device to operate as medical device programmer 14. A wireless adapter coupled to the computing device may enable secure communication between the computing device and IMD 16.

Programmer 14 may also be configured for use by patient 12, e.g., to select therapy programs and/or view and modify electrical stimulation parameters. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain electrical stimulation parameters or set an available range of values for a particular electrical stimulation parameter.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

Programmer 14 may also provide an indication to patient 12 when therapy is being delivered, when patient input has triggered a change in electrical stimulation parameters or when the power source within programmer 14 or IMD 16 needs to be replaced or recharged. For example, programmer 14 may include an alert LED, may flash a message to patient 12 via a programmer display, or may generate an audible sound or somatosensory cue to confirm patient input was received, e.g., to indicate a patient state or to manually modify an electrical stimulation parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth™ specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

DBS system 10 may be implemented to provide chronic stimulation therapy to patient 12 over the course of several months or years. However, DBS system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to deliver electrical stimulation to the GPe of brain 13 of patient 12. Systems with other configurations of leads, electrodes, and sensors are possible. For example, in other implementations, IMD 16 may be coupled to additional leads or lead segments. The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. As another example configuration, system 10 can include one or more microstimulators in addition to, or instead of, IMG 16 and lead 20. The microstimulators can have a smaller form factor than IMD 16 and may not be coupled to any leads. Rather, the microstimulators can be leadless and configured to generate and deliver electrical stimulation therapy to the GPe (and one or more other regions of brain 13 in some examples) via one or more electrodes on an outer housing of the microstimulators. IMD 16 or another microstimulator may act as a "master" module that coordinates the delivery of stimulation to patient 12 via the plurality of microstimulators.

Figure 2:
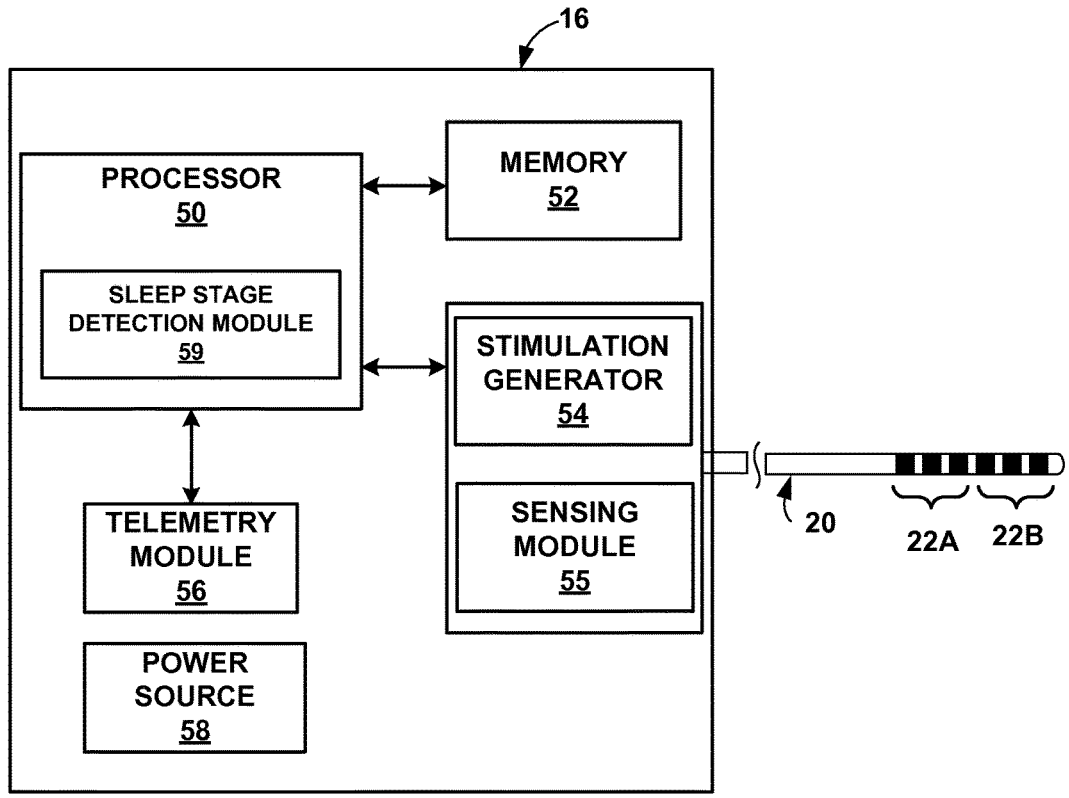
FIG. 2 is a functional block diagram illustrating components of an example medical device.

FIG. 2 is a functional block diagram illustrating components of an example IMD 16. In the example shown in FIG. 2, IMD 16 generates and delivers electrical stimulation therapy to patient 12. IMD 16 includes processor 50, memory 52, stimulation generator 54, sensing module 55, telemetry module 56, power source 58, and sleep stage detection module 59. Although sleep stage detection module 59 is shown to be a component of processor 50 in FIG. 2, in other examples, sleep stage detection module 59 and processor 50 may be separate components and may be electrically coupled, e.g., via a wired or wireless connection.

Memory 52 may include any volatile or non-volatile media, such as a random access memory (RAM), read only memory (ROM), non-volatile RAM (NVRAM), electrically erasable programmable ROM (EEPROM), flash memory, and the like, as well as combinations thereof. Memory 52 may store instructions for execution by processor 50 and information defining delivery of electrical stimulation to patient 12, such as, but not limited to, therapy programs (e.g., sets of stimulation parameter values) or therapy program groups, information associating therapy programs with one or more sleep stages, thresholds or other information used to detect a sleep state, movement state, and specific sleep stages based on biosignals, information regarding biosignals of target tissue sites of patient 12, and any other information regarding therapy of patient 12. Therapy information may be recorded in memory 52 for long-term storage and retrieval by a user. As described in further detail with reference to FIG. 3, memory 52 may include separate memories for storing information, such as separate memories for therapy programs, sleep stage information, diagnostic information, target tissue site information, and patient information. In some examples, memory 52 stores program instructions that, when executed by processor 50, cause IMD 16 and processor 50 to perform the functions attributed to them herein.

Processor 50 controls stimulation generator 54 to generate and deliver electrical stimulation therapy via lead 20. An example range of electrical stimulation parameter values that may provide efficacious electrical stimulation to a GPe of brain 13 (FIG. 1) to manage a sleep disorder may include:

1. Frequency: between approximately 20 Hz and approximately 300 Hz, such as approximately 80 Hz.
2. Amplitude: between approximately 0.1 microamps and approximately 200 microamps, such as approximately 100 microamps. In other examples, rather than a current controlled system, IMD 16 may control the voltage.
3. Pulse Width: between approximately 10 microseconds and approximately 5000 microseconds, such as between approximately 50 microseconds and approximately 1000 microseconds.

An example range of electrical stimulation parameter values that may define efficacious electrical stimulation therapy delivered to a STN or GPe or GPi of brain 13 to manage a movement disorder of patient 12 may include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts. In other examples, rather than a voltage controlled system, IMD 16 may control the current.
3. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.
4. Pulse Width: between approximately 10 microseconds and approximately 5000 microseconds, such as between approximately 100 microseconds and approximately 1000 microseconds, or between approximately 180 microseconds and approximately 450 microseconds.

Other therapy parameter values may also be useful. While stimulation pulses are described, stimulation signals may be of any form, such as continuous-time signals (e.g., sine waves) or the like.

As described in further detail below, processor 50 can control stimulation generator 54 to generate stimulation that is delivered to the GPe of brain 13 of patient 12 and at least one of the STN or the GPi of brain 13 according to the stimulation parameter values of different therapy programs. In each of the examples described herein, if stimulation generator 54 shifts the delivery of stimulation energy between two therapy programs, processor 50 of IMD 16 may provide instructions that cause stimulation generator 54 to time-interleave stimulation energy between the electrode combinations of the two therapy programs, as described in U.S. Pat. No. 7,519,431 issued to Steven Goetz et al. on Apr. 14, 2009, entitled "SHIFTING BETWEEN ELECTRODE COMBINATIONS Ind. ELECTRICAL STIMULATION DEVICE," the entire content of which is incorporated herein by reference.

In some examples, stimulation generator 54 is configured such that each electrode 22 is associated with its own current source. Processor 50 may also control delivery of electrical stimulation to patient 12 by controlling stimulation generator 54 to deliver electrical stimulation to one target tissue site with particular subset of electrodes (e.g., electrodes 22A of DBS system 10) and to another target tissue site with a different subset of electrodes (e.g., electrodes 22B of DBS system 10). For example, stimulation generator 54 may deliver electrical stimulation to the GPe of brain 13 of patient 12 via electrodes 22A and to at least one of the STN or the GPi of brain 13 of patient 12 via electrodes 22B. In some cases, electrical stimulation may be delivered via electrodes 22A according to a particular therapy program and via electrodes 22B according to a different therapy program (e.g., defining at least one different stimulation parameter value than the therapy program delivered via electrodes 22A to the subthalamic nucleus). Processor 50 may independently control electrical stimulation via electrodes 22A and 22B, such that the stimulation may be simultaneously or at different times (e.g., alternatively). In other examples, processor 50 may control delivery of electrical stimulation by controlling stimulation generator 54 to deliver electrical stimulation to several different target tissue sites with some or all of the same electrodes.

Processor 50 can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed to processor 50 herein may be embodied as firmware, hardware, software or any combination thereof. In general, components described as processors within IMD 16, external programmer 14 or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and embodied as software, firmware, hardware, or any combination thereof.

Sleep stage detection module 59 is configured to determine a current sleep stage of patient 12 based on a sensed biosignal. In some examples, sleep stage detection module 59 may be coupled to sensing module 55, which generates a signal indicative of electrical activity within brain 13 of patient 12. In this way, sensing module 55 may detect or sense a biosignal within brain 13 of patient 12. Example electrical signals that sensing module 55 may sense include, but are not limited to, a signal generated from local field potentials within one or more regions of brain 13. EEG and ECoG signals are examples of local field potentials that may be measured within brain 13. However, local field potentials may include a broader genus of electrical signals within brain 13 of patient 12. Sensing module 55 can also be configured to generate an electrical signal indicative of other physiological parameters of patient 12.

Although sensing module 55 is incorporated into a common housing with stimulation generator 54 and processor 50 in FIG. 2, in other examples, sensing module 55 may be in a separate housing from IMD 16 and may communicate with processor 50 via wired or wireless communication techniques.

Figure 6:
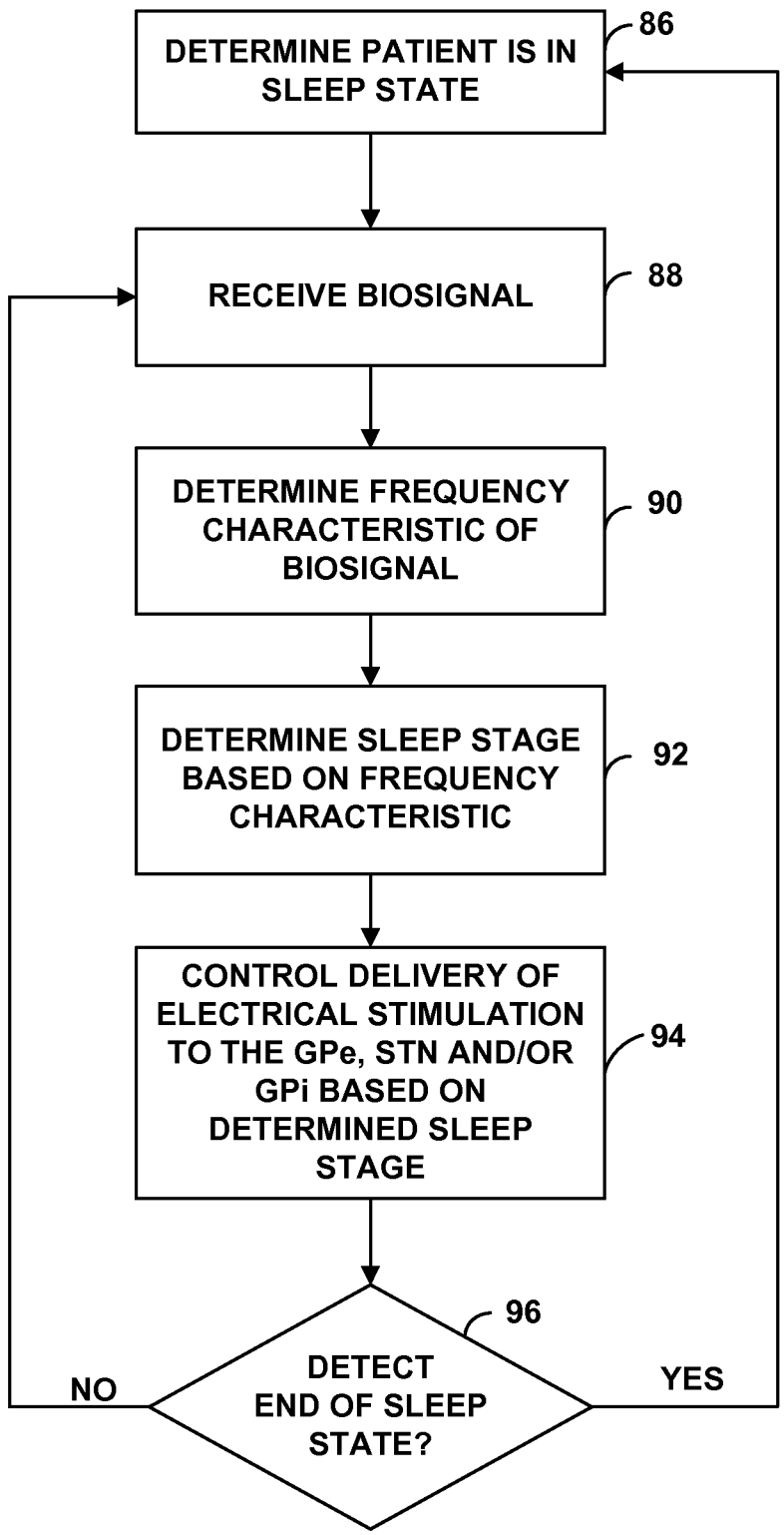
FIG. 6 is a flow diagram illustrating an example technique for controlling therapy delivery to a brain of a patient based on a determined patient sleep stage.

As described in further detail with respect to FIG. 6, processor 50 can determine a current sleep stage of patient 12 based on a biosignal sensed by sensing module 55. In some examples, sensing module 55 generates a signal indicative of brain activity of patient 12 (e.g., by determining tissue potentials across electrodes 22), and sleep stage detection module 59 analyzes the signal to determine a current sleep stage of patient 12. In addition to or instead of monitoring biosignals of patient 12 via electrodes 22 coupled to lead 20, sleep stage detection module 59 may directly or indirectly receive biosignals indicative of electrical activity within brain 13 from electrodes coupled to another lead that is electrically coupled to sensing module 55, biosignals from electrodes coupled to an outer housing of IMD 16 and electrically coupled to sensing module 55, and/or biosignals from a sensing module that is separate from IMD 16.

In response to determining the patient's current sleep stage, sleep stage detection module 59 may generate a sleep stage indication. The sleep stage indication may be a value, flag, or signal that is stored or transmitted to indicate the current sleep stage of patient 12. In some examples, sleep stage detection module 59 may transmit the sleep stage indication to another device, such as programmer 14, via telemetry module 56.

In some examples, processor 50 may control delivery of electrical stimulation to the GPe of brain 13 of patient 12 based on the sleep stage indication. In other examples, processor 50 controls stimulation generator 54 to deliver electrical stimulation to the GPe independent of the particular sleep stage of patient 12. For example, processor 50 may control stimulation generator 54 to deliver electrical stimulation to the GPe substantially continuously or periodically (e.g., according to a predetermined schedule, which may be stored by memory 52). In examples in which stimulation generator 54 delivers electrical stimulation to the GPe independent of the particular sleep stage of patient 12, stimulation generator 54 may generate the electrical stimulation in accordance with one therapy program stored by memory 54 or in accordance with a plurality of different therapy programs. For example, different therapy programs may be associated with different times (e.g., measured relative to the beginning of the sleep state, as determined by when processor 50 first detects the sleep state), and a stored schedule may associate a plurality of different times during the sleep state with respective therapy programs, which may or may not be the same as each other.

In addition, in some examples in which IMD 16 is configured to deliver electrical stimulation to at least one of the STN or the GPi, processor 50 may control delivery of electrical stimulation to the at least one of the STN or GPi of brain 13 of patient 12 based on the sleep stage indication, as described in further detail below with respect to FIG. 6.

In some examples, processor 50 may select one or more therapy programs from memory 52 or modify one or more of the stimulation parameter values of one or more stored therapy programs based on the sleep stage indication generated by sleep stage detection module 59 and control the delivery of electrical stimulation in accordance with the modified one or more stimulation parameter values. Alternatively, processor 50 may select one or more therapy programs from memory 52 (e.g., by selecting a stored therapy program or selecting instructions reflecting modifications to a stored therapy program) and transmit the selected therapy program(s) to processor 50, which may then control stimulation generator 54 to deliver therapy according to the selected therapy program(s).

The "selected" therapy program(s) may include, for example, a stored program selected from memory 52 based on the determined sleep stage or a predetermined schedule, a stored therapy program and instructions indicating modifications to be made to a stored therapy program based on the determined sleep stage or a predetermined schedule, a stored therapy program that has already been modified, or indicators associated with any of the aforementioned therapy programs (e.g., alphanumeric indicators associated with the therapy program). In some examples, processor 50 may record information relating to the sleep stage indication, e.g., the date and time of the particular patient state, in memory 52 for later retrieval and analysis by a clinician.

Processor 50 controls telemetry module 56 to send and receive information. Telemetry module 56 in IMD 16, as well as telemetry modules in other devices and systems described herein, such as programmer 14, may accomplish communication by RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request from IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
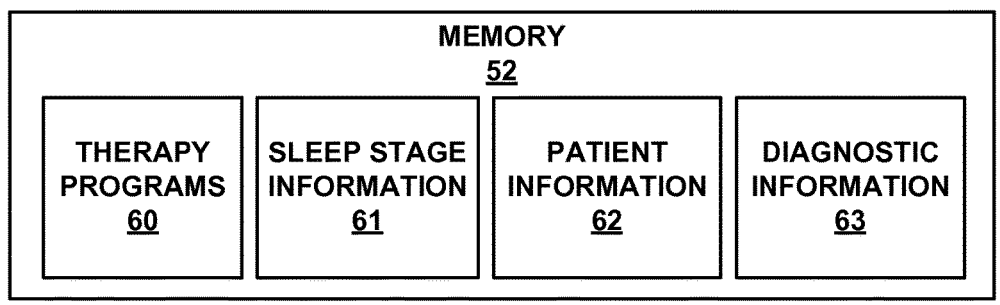
FIG. 3 is a functional block diagram illustrating an example configuration of a memory of a medical device.

FIG. 3 is a block diagram illustrating an example configuration of memory 52 of IMD 16. In the example of FIG. 3, memory 52 stores therapy programs 60, sleep stage information 61, patient information 62, and diagnostic information 63.

Therapy programs 60 may store a plurality of therapy programs as respective records that are stored in a table or other data structure that associates therapy programs or electrical stimulation parameter values with one or more times (in accordance with a predetermined schedule), or one or more sleep stages (e.g., Stage 1, Stage 2, Deep Sleep or REM) and/or frequency domain characteristics of a biosignal (e.g., threshold values or templates), which may be associated with respective sleep stages. While the remainder of the disclosure refers primarily to tables, the present disclosure also applies to other types of data structures that store therapy programs or electrical stimulation parameter values and associated physiological parameters.

In the case of electrical stimulation therapy, each of the programs in therapy programs 60 may include respective values for a plurality of therapy parameters, such as voltage or current amplitude, signal duration, frequency, pulse width and electrode configuration (e.g., an indication of the electrodes 22 selected to deliver stimulation and the respective polarity of the electrodes). In some examples, in response to detecting the sleep state, processor 50 of IMD 16 may select one or more therapy programs from the stored therapy programs 60 associated with the sleep state. In addition, or instead, processor 50 may select one or more programs from the stored therapy programs 60 according to a predetermined schedule. In addition, or instead, processor 50 may select one or more programs from the stored therapy programs 60 based on a sleep stage determined at least in part based on a biosignal sensed within brain 13 of patient 12.

The therapy programs stored in programs 60 may be generated using programmer 14, e.g., during an initial or follow-up programming session, and received by processor 50 from programmer 14 via telemetry module 56. Therapy programs 60 may associate electrical stimulation parameter values or instructions for modifying a baseline therapy program with the sleep state, a particular sleep stage, or a particular part of a schedule. In this manner, processor 50 can control electrical stimulation by activating, deactivating, increasing an intensity, or decreasing an intensity of electrical stimulation achieved by selecting a therapy program from the stored therapy programs 60 or selecting instructions for modifying a therapy program.

In other examples, programmer 14 may store therapy programs 60, and processor 50 of IMD 16 may receive selected programs from programmer 14 via telemetry circuit 56.

Sleep stage information 61 may store information associating various sleep stage indicators, e.g., biosignals and, in some cases, a physiological signal indicative of a physiological parameter of patient 12 other than brain activity, with a respective sleep stage. For example, sleep stage information 61 may store a plurality of threshold values or templates, where each threshold value or template may correspond to at least one type of sleep stage. The threshold values may be, for example, threshold power levels within selected frequency bands of a biosignal that indicate a particular sleep stage, or values that are generated based on ratios of power between two or more frequency bands. The thresholds may be patient specific or may be generally applicable to more than one patient. The template may be, for example, a waveform template or a pattern in power levels of the biosignal within a selected frequency band over time. Sleep stage detection module 59 may access sleep stage information 61 to determine, based on the threshold values or templates, whether a detected biosignal is indicative of a particular sleep stage.

Patient information portion 62 of memory 52 may store data relating to patient 12, such as the patient's name and age, the type of IMD 16 or leads 20 implanted within patient 12, medication prescribed to patient 12, and the like. Processor 50 of IMD 16 may also collect diagnostic information 63 and store diagnostic information 63 within memory 52 for future retrieval by a clinician. Diagnostic information 63 may, for example, include selected recordings of the output of sensing module 55 or sleep stage indications generated by sleep stage module 59. In some examples, diagnostic information 63 may include information identifying the time at which the different sleep stages occurred. A clinician may later retrieve the information from diagnostic information 63 and determine a length of one or more of the patient's sleep stages based on this information.

Diagnostic information 63 may include other information or activities indicated by patient 12 using programmer 14, such as changes in symptoms, medication ingestion, or other activities of patient 12. A clinician may review diagnostic information 63 in a variety of forms, such as timing diagrams or a graph resulting from statistical analysis of diagnostic information 63, e.g., a bar graph. The clinician may, for example, download diagnostic information 63 from IMD 16 via programmer 14 or another computing device. Diagnostic information 63 may also include calibration routines for electrodes 22 (FIG. 1) and malfunction algorithms to identify stimulation dysfunctions.

Figure 4:
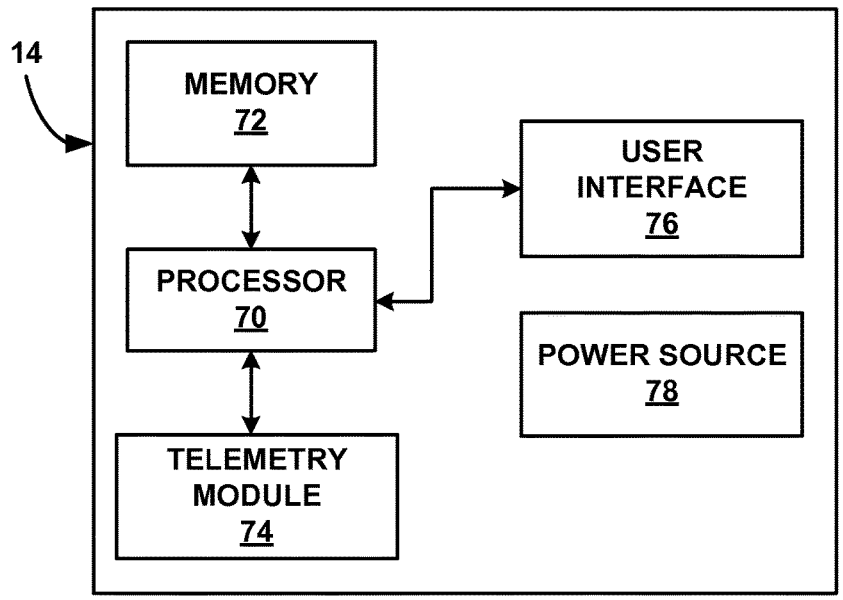
FIG. 4 is a functional block diagram illustrating components of an example medical device programmer.

FIG. 4 is a conceptual block diagram of an example external medical device programmer 14, which includes processor 70, memory 72, telemetry module 74, user interface 76, and power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

Processor 70 monitors activity from the input controls and controls the display of user interface 76. The user, such as a clinician or patient 12, may interact with programmer 14 through user interface 76. User interface 76 may include a display (not shown), such as an LCD or other type of screen, to present information related to the therapy, and input controls (not shown) to provide input to programmer 14. Input controls may include buttons, a keypad (e.g., an alphanumeric keypad), a peripheral pointing device, or another input mechanism that allows the user to navigate though the user interface of programmer 14 and to provide input. If user interface 76 includes buttons and a keypad, the buttons may be dedicated to performing a certain function, i.e., a power button, or the buttons and the keypad may be soft keys that change in function depending upon the section of the user interface currently viewed by the user. Alternatively, the display screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or sounds to patient 12 and/or receiving voice commands from patient 12, which may be useful if patient 12 has limited motor functions.

In some examples, at least some of the control of therapy delivery by IMD 16 may be implemented by processor 70 of programmer 14. For example, some examples, processor 70 may control stimulation generator 54 of IMD 16 to deliver electrical stimulation therapy to the GPe of brain 13 of patient 12, e.g., in response to detecting a sleep state of patient 12 or in response to detecting a specific sleep stage of the sleep state. In some examples, processor 70 may receive a biosignal from IMD 16 or from a sensing module that is separate from IMD 16, where the biosignal is sensed within brain 13 by IMD 16 or the sensing module that is separate from IMD 16. The separate sensing module may, but need not be, implanted within patient 12. In some examples, processor 70 may determine the current sleep stage of patient 12 based on the detected biosignal and may transmit a signal to IMD 16 via telemetry module 74, to indicate the determined sleep stage. For example, processor 70 may include a sleep stage detection module similar to sleep stage detection module 59 (FIG. 2) of IMD 16. Processor 50 of IMD 16 may receive the signal from programmer 14 via its respective telemetry module 56 (FIG. 3).

In some examples, such as examples in which IMD 16 delivers electrical stimulation to the GPe or at least one of the STN or GPi based on a determined sleep stage, processor 50 of IMD 16 may select one or more stored therapy programs from memory 52 based on the current sleep stage. Alternatively, processor 70 of programmer 14 may select a therapy program and transmit a signal to IMD 16, where the signal indicates the therapy parameter values to be implemented by IMD 16 during the therapy delivery to help improve the patient's sleep quality, or may provide an indication of the selected therapy program that is stored within memory 52 of IMD 16. The indication may be, for example, an alphanumeric identifier or symbol that is associated with the therapy program in memory 52 of IMD 16.

Patient 12, a clinician or another user may also interact with programmer 14 to manually select therapy programs, generate new therapy programs, modify therapy programs through individual or global adjustments, and transmit the new programs to IMD 16. In a learning mode, programmer 14 may allow patient 12 and/or the clinician to determine which therapy programs are best suited for one or more specific sleep stages and for the awake patient state.

Memory 72 may include instructions for operating user interface 76, telemetry module 74 and managing power source 78. Memory 72 may also store any therapy data retrieved from IMD 16 during the course of therapy. The clinician may use this therapy data to determine the progression of the patient condition in order to configure future treatment. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to telemetry module 56 of IMD 16. In alternative examples, programmer 14 may be capable of infrared communication or direct communication through a wired connection. In this manner, other external devices may be capable of communicating with programmer 14 without needing to establish a secure wireless connection.

Power source 78 delivers operating power to the components of programmer 14. Power source 78 may include a battery and a power generation circuit to produce the operating power. In some examples, the battery may be rechargeable to allow extended operation.

Figure 5:
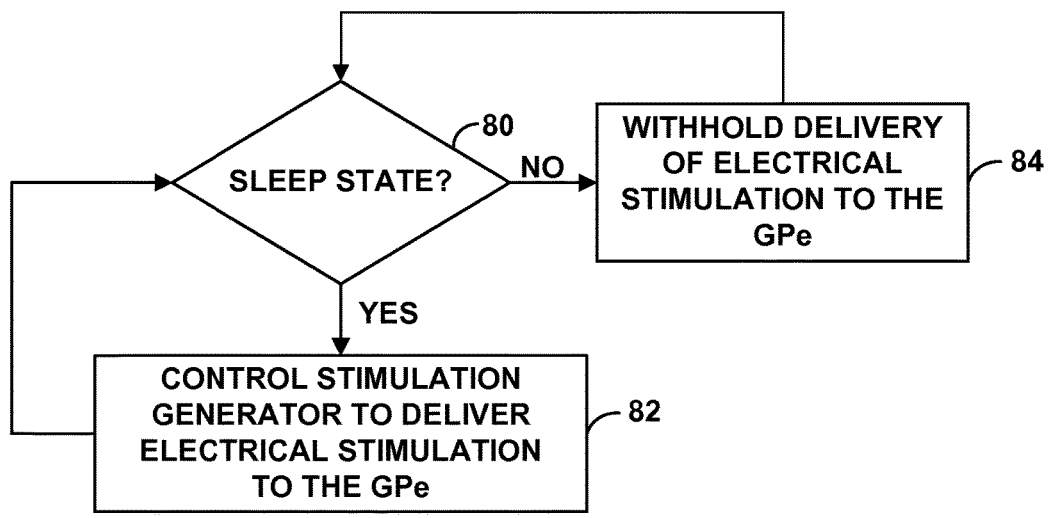
FIG. 5 is a flow diagram illustrating an example technique for controlling therapy delivery to an external portion of a globus pallidus of a brain of a patient.
Figure 7:
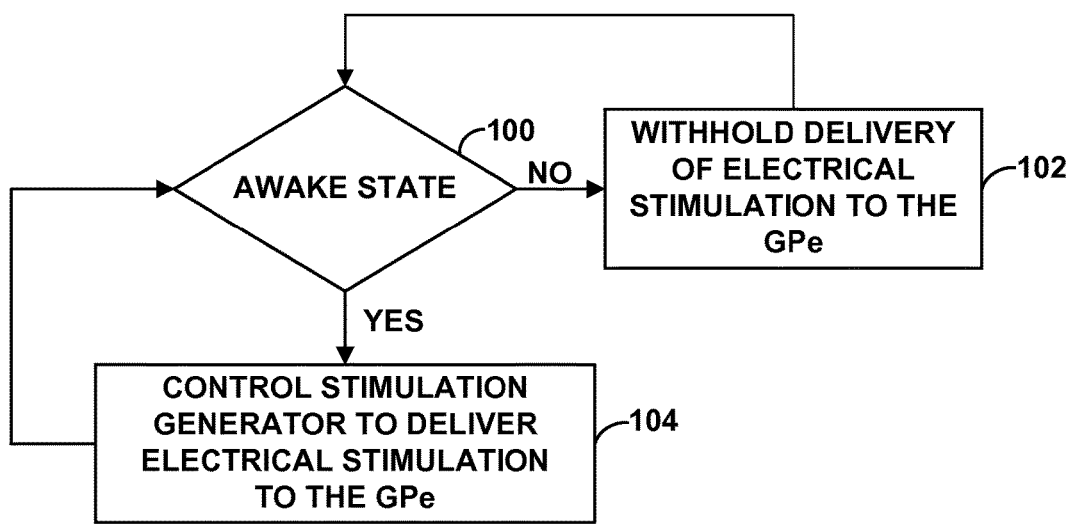
FIG. 7 is a flow diagram illustrating another example technique for controlling therapy delivery to an external portion of a globus pallidus of a brain of a patient.

FIG. 5 is a flow diagram illustrating an example technique for controlling delivery of electrical stimulation to a GPe of brain 13 of patient 12 by IMD 16. While the techniques shown in FIGS. 5-7 are primarily described as being performed by processor 50 of IMD 16, in other examples, a processor of another device, such as processor 70 of programmer 14, can perform any part of the techniques shown in FIGS. 5 and 6, alone or in combination with processor 50.

In accordance with the technique shown in FIG. 5, processor 50 determines whether patient 12 is in a sleep state (80). In some examples, processor 50 receives input from a user (e.g., patient 12, a patient caretaker, or another user) that indicates patient 12 is commencing the sleep state (e.g., attempting to sleep), is asleep, or is otherwise in the sleep state. The user can provide the input using any suitable mechanism. For example, the user can provide the input via user interface 76 of programmer 14, and, in response to receiving the user input via user interface 76, processor 70 of programmer 14 may transmit a signal indicative of the user input to processor 50 of IMD 16 via the respective telemetry modules 74, 56. As another example, the user may interact directly with IMD 16 to provide the input. For example, a motion sensor can be integrated into or on a housing of IMD 16, and the motion sensor can generate a signal that is indicative of patient 12 tapping IMD 16 through the skin. The number, rate, or pattern of taps may be associated with the user input indicative of a sleep state, and processor 50 may identify the tapping by patient 12 to determine when patient input is received.

In other examples, processor 50 determines patient 12 is in the sleep state (also referred to herein as "detecting" a sleep state) based on a sensed patient parameter. For example, processor 50 may determine patient 12 is in the sleep state based on a bioelectrical brain signal sensed by sensing module 55. Memory 52 may, for example, store one or more signal characteristics indicative of a sleep state and processor 50 may determine patient 12 is in the sleep state in response to determining a bioelectrical brain signal sensed by sensing module 55 includes the one or more signal characteristics. The one or more signal characteristics can include, for example, a time domain characteristic such as an amplitude or amplitude waveform, or a frequency domain characteristic, such as a power level (or energy) within one or more frequency bands of the biosignal, a ratio of the power level in two or more frequency bands, a correlation in change of power between two or more frequency bands, a pattern in the power level of one or more frequency bands over time, and the like.

As another example of determining a sleep state based on a sensed patient parameter, processor 50 may detect the sleep state based on an activity level or posture level of patient, based on values of one or more physiological parameters, or both. Examples of physiological parameters that may indicate a sleep state or sleep stage include, for example, a heart rate, a respiration rate, a respiratory volume, a blood pressure, a blood oxygen saturation, a partial pressure of oxygen within blood, a partial pressure of oxygen within cerebrospinal fluid, muscular activity, a core temperature, an arterial blood flow, and a galvanic skin response.

For example, processor 50 may detect when patient 12 is in sitting or lying down based on an output generated by a motion sensor (e.g., an accelerometer, a bonded piezoelectric crystal, a mercury switch or a gyro) that indicates patient posture, an patient activity level, or both, and determine patient 12 is in a sleep state in response to detecting a relatively low activity level. The motion sensor can be incorporated into an outer housing of IMD 16 or may be external to IMD 16, such as external to patient 12 or implanted in patient 12 separately from IMD 16.

Example techniques for determining a patient's activity level or posture are described in commonly-assigned U.S. Patent Application Publication No. 2005/0209644, entitled, "COLLECTING ACTIVITY INFORMATION TO EVALUATE THERAPY," and U.S. patent application Ser. No. 11/799,035, entitled, "THERAPY ADJUSTMENT." U.S. Patent Application Publication No. 2005/0209644 and U.S. patent application Ser. No. 11/799,035 are incorporated herein by reference in their entireties. As described in U.S. Patent Application Publication No. 2005/0209644, a processor may determine an activity level based on a signal from a motion sensor, such as an accelerometer, a bonded piezoelectric crystal, a mercury switch or a gyro, by sampling the signal and determining a number of activity counts during the sample period. For example, processor 50 may compare the sample of a signal generated by an accelerometer or piezoelectric crystal to one or more amplitude thresholds stored within memory 52. Processor 50 may identify each threshold crossing as an activity count. Where processor 50 compares the sample to multiple thresholds with varying amplitudes, processor 50 may identify crossing of higher amplitude thresholds as multiple activity counts. In some examples, processor 50 may determine patient 12 is in a sleep state based on the activity counts within a particular timeframe being less than or equal to a sleep threshold.

In another example, processor 50 may detect the sleep state based on values of one or more sleep metrics that indicate a probability of patient 12 being asleep, such as using the techniques described in commonly-assigned U.S. Patent Application Publication No. 2005/0209512 by Heruth et al., entitled "DETECTING SLEEP," which was filed on Apr. 15, 2004 or commonly-assigned U.S. Pat. No. 7,491, 181 to Heruth et al., entitled, "COLLECTING ACTIVITY AND SLEEP QUALITY INFORMATION VIA A MEDICAL DEVICE," which was issued on Feb. 17, 2009. The entire content of U.S. Patent Application Publication No. 2005/0209512 by Heruth et al. and U.S. Pat. No. 7,491,181 to Heruth et al. is incorporated herein by reference.

As described in U.S. Patent Application Publication No. 2005/0209512, a sensor that is incorporated with IMD 16, or, in some examples, a separate sensor, may generate a signal as a function of at least one physiological parameter of a patient that may discernibly change when the patient is asleep. Examples of physiological parameters that may alone or in any suitable combination indicate a sleep state include, for example, an activity level, a patient posture, a heart rate, a respiration rate, a respiratory volume, a blood pressure, a blood oxygen saturation, a partial pressure of oxygen within blood, a partial pressure of oxygen within cerebrospinal fluid, muscular activity, a core temperature, an arterial blood flow, and galvanic skin response. In some examples, processor 50 of IMD 16 may determine a value of a sleep metric that indicates a probability of the patient being asleep based on a physiological parameter. In particular, processor 50 (or processor 70 of programmer 14) may apply a function or look-up table to the current value and/or variability of the physiological parameter to determine the sleep metric value. Processor 50 may compare the sleep metric value to a threshold value to determine whether the patient is in the sleep state. In some examples, the probability may be more than just an indication of "sleep state" or "awake state" but may include an indication of the probability, e.g., between 1% to about 100%, that patient 12 is in a sleep state.

In addition to or instead of detecting a sleep state based on patient input or a physiological parameter of patient 12, processor 50 may detect the sleep state (80) based on a time schedule, which may be stored in memory 52 of IMD 16. The schedule may be selected by a clinician or IMD 16 may learn the schedule based on past patient inputs or other determinations. The schedule may set forth the times of a day in which patient 12 is typically in an awake state (e.g., not in a sleep state) and/or in a sleep state. For example, the schedule may be generated based on a circadian rhythm that is specific to patient 12. Processor 50 may track the time of day with a clock, which may be included as part of processor 50 or as a separate component within IMD 16. In some examples, processor 50 may automatically implement a clock based on a circadian rhythm of a typical patient, i.e., a generic circadian rhythm, rather than a circadian rhythm that is specific to patient 12.

In response to determining patient 12 is in a sleep state ("YES" branch of block 80), processor 50 controls stimulation generator 54 to deliver electrical stimulation to the GPe (82). In some examples, processor 50 controls stimulation generator 54 to deliver electrical stimulation substantially continuously (e.g., continuously or nearly continuously) to the GPe during the sleep state. In other examples, processor 50 controls stimulation generator 54 to deliver electrical stimulation to the GPe periodically during the sleep state (e.g., according to a predetermined schedule or cycle). The electrical stimulation delivered to the GPe may be configured to help address a sleep impairment of patient 12, such as by regulating the sleep of patient 12 (e.g., by helping patient 12 stay asleep and reducing the number of transitions between being asleep and awake), by reducing the sleep latency of patient 12, or both. Thus, delivering the electrical stimulation to the GPe, via stimulation generator 54, during the sleep state and not in response to a particular sleep stage detection may provide therapeutic effects. However, in some examples, processor 50 controls stimulation generator 54 to deliver electrical stimulation to the GPe in response to detecting a specific sleep stage of the sleep state, as discussed in further detail with respect to FIG. 6.

Processor 50 controls stimulation generator 54 to deliver electrical stimulation to the GPe (82) until processor 50 determines that patient 12 is not in a sleep state. As shown in FIG. 5, in response to determining patient 12 is not in a sleep state ("NO" branch of block 80), processor 50 controls stimulation generator 54 to withhold the delivery of electrical stimulation to the GPe (84). However, in some examples, processor 50 may control stimulation generator 54 to deliver other electrical stimulation to the GPe in response to determining patient 12 is not in a sleep state, such as electrical stimulation configured to help another patient condition or to help patient 12 maintain an awake state.

For example, if stimulation generator 54 was delivering electrical stimulation to the GPe, processor 50 may control stimulation generator 54 to terminate all delivery of electrical stimulation to the GPe or at least the electrical stimulation that is configured to help patient 12 fall asleep or stay asleep. As another example, if stimulation generator 54 was not actively delivering electrical stimulation to the GPe, then processor 50 may control stimulation generator 54 to withhold any further delivery of electrical stimulation to the GPe (84) until the sleep state is detected or at least withhold the delivering of electrical stimulation to the GPe that is configured to help patient 12 fall asleep or stay asleep (80).

As discussed above, the delivery of electrical stimulation to the GPe may be used to treat a sleep impairment of patient 12 alone or in combination with other therapies. For example, processor 50 can also control stimulation generator 54 to deliver electrical stimulation to the STN, GPi, or both, of brain 13, where the electrical stimulation is configured to help treat a movement disorder of patient 12. Processor 50 can be configured to independently control the delivery of electrical stimulation to the GPe and the at least one of the STN and the GPi, such that the delivery of electrical stimulation to the GPe can occur at a different time, based on different therapy parameter values, or both, than the delivery of electrical stimulation to the STN or the GPi. In addition, in some examples, processor 50 can be configured to independently control the delivery of electrical stimulation to the STN and the GPi, such that the delivery of electrical stimulation to the STN can occur at a different time, based on different therapy parameter values, or both, than the delivery of electrical stimulation to the GPi.

Due to the proximity of the GPe, the STN, and the GPi within brain 13 of patient 12, a common lead 20 can be used to deliver electrical stimulation to both the GPe and at least one of the STN or the GPi. The use of one lead to independently deliver stimulation to the GPe and at least one of the STN or the GPi can provide certain advantages, such as minimizing the invasiveness of DBS system 10. In addition, in some examples, electrodes 22 are arranged on lead 20 (e.g., axially spaced from each other along the longitudinal axis of lead 20) such that once electrodes 22A are located in the GPe, e.g., as indicated by biosignals sensed with electrodes 22A, there is a high likelihood that electrodes 22B are properly positioned in the STN, GPi, or both. In other examples, electrodes 22 are arranged on lead 20 such that once electrodes 22B are located in the STN, GPi, or both, there is a high likelihood that electrodes 22A are properly positioned in the GPe.

In other examples, however, multiple leads can be used to deliver stimulation to the GPe and at least one of the STN or the GPi. For example, separate leads can deliver stimulation to a respective one of the GPe and the at least one of the STN or the GPi, whereby the separate leads can be coupled to a common IMD 16 or separate IMDs. In addition, in some examples, one or more self-contained medical devices (e.g., a microstimulator) that include electrodes on an outer housing of the medical device can be used to independently deliver stimulation to the GPe and at least one of the STN or GPi.

Electrical stimulation of the GPe and at least one of the STN and GPi may provide effective therapy for a sleep disorder of patient 12. Simultaneously but independently controlling electrical stimulation of both the GPe and at least one of the STN and GPi may result in increased quality of sleep for patient 12. The GPe may play a role in sleep regulation and the STN and GPi may play roles in movement control.

While delivery of stimulation to the STN via a subset of electrodes may deliver incidental electrical stimulation to the GPe, or vice versa, the incidental electrical stimulation may not have a sufficient intensity to generate physiological effects. For example, delivery of stimulation to the STN, GPi, or both, via one subset of electrodes may generate an electrical field that covers at least a part of the GPe, but the portion of the electrical field that overlaps with the GPe may be insufficient to activate the neurons within the GPe and modulate activity in the GPe. Similarly, delivery of stimulation to the GPe via a second subset of electrodes different than the first subset (differing by at least one electrode) may result in incidental stimulation to the STN or the GPi, but the incidental stimulation may not be of sufficient intensity to generate physiological effects and modulate activity within the STN or the GPi, e.g., because the electrical field resulting from the delivery of electrical stimulation to the GPe may be insufficient to activate the neurons within the STN and GPi.

FIG. 6 is a flow diagram illustrating an example technique for controlling delivery of electrical stimulation by IMD 16 based on a determination of a sleep stage of patient 12. In accordance with the technique shown in FIG. 6, processor 50 determines patient 12 is in a sleep state (86) using any suitable technique, such as those as described with respect to block 80 in FIG. 5. Processor 50 receives a biosignal indicative of activity within brain 13 of patient 12 (88), e.g., from sensing module 55 (FIG. 2) or a separate sensing module that senses the biosignal within brain 13 of patient 12. Sleep stage detection module 59, or, more generally, processor 50, may determine a frequency characteristic of the biosignal (90). In some examples, processor 50 may receive the biosignal prior to determining the sleep state. Thus, the technique shown in FIG. 6 is not limited to receiving the biosignal after detecting the sleep state. In some examples, processor 50 may continuously receive the biosignal (88) from sensing module 55 or at periodic intervals, which may be set by a clinician. For example, processor 50 may periodically interrogate sensing module 55 to receive the biosignal (88). As another example, sensing module 55 may periodically transmit the biosignal to processor 50, such as at a frequency of about 0.1 Hz to about 100 Hz.

In the example shown in FIG. 6, sleep stage detection module 59 determines a sleep stage of patient based on a frequency band characteristic of the biosignal that is indicative of activity within brain 13 of patient 12 (92). An example technique for determining a sleep stage of patient based on a frequency band characteristic of the biosignal is described in U.S. Patent Application Publication No. 2009/0192556 by Wu et al. (published on Jul. 30, 2009), which is entitled, "SLEEP STAGE DETECTION" and is incorporated herein by reference in its entirety.

Sleep stage detection module 59 (FIG. 2) may determine a frequency band characteristic of the biosignal (90) using any suitable technique. The frequency characteristic may include, for example, at least one of a power level (or energy) within one or more frequency bands of the biosignal, a ratio of the power level in two or more frequency bands, a correlation in change of power between two or more frequency bands, or a pattern in the power level of one or more frequency bands over time. In one example, sleep stage detection module 59 may comprise an amplifier that amplifies a received biosignal and a bandpass or a low pass filter that filters the monitored biosignal to extract one or more selected frequency bands of the biosignal. The extracted frequency bands may be selected based on the frequency band that is revealing of the one or more sleep stages that are being detected. Sleep stage detection module 59 may then determine the frequency characteristic based on the extracted frequency band component of the biosignal.

As described in U.S. Patent Application Publication No. 2009/0192556 by Wu et al., different frequency bands are associated with different activity in brain 13. It is believed that some frequency band components of a biosignal from within brain 13 may be more revealing of particular sleep stages than other frequency components. One example of the frequency bands is shown in Table 2:

TABLE 1

| Frequency bands | |
| --- | --- |
| Frequency (f) Band Hertz (Hz) | Frequency Information |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 2 are merely examples. The frequency ranges may differ in other examples. For example, another example of frequency ranges for frequency bands are shown in Table 3:

TABLE 2

| Frequency bands | |
| --- | --- |
| Frequency (f) Band Hertz (Hz) | Frequency Information |
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

Processor 50 may select a frequency band for determining the patient sleep stage using any suitable technique. In one example, the clinician may select the frequency band based on information specific to patient 12 or based on data gathered from more than one patient 12. The frequency bands that are useful for distinguishing between two or more different patient sleep stages or otherwise determining a patient sleep stage based on a biosignal from brain 13 may differ between patients. In some examples, a clinician may calibrate the frequency ranges to a specific patient based on, for example, a sleep study. During the sleep study, the clinician may monitor a biosignal and determine which, if any, frequency bands or ratio of frequency bands exhibit a characteristic that helps to detect a sleep stage and/or distinguish between different sleep stages.

Sleep stage detection module 59 (FIG. 2) may determine a sleep stage based on the frequency characteristic of the biosignal (92). In some techniques, sleep stage detection module 59 may compare the frequency characteristic to one or more threshold values in order to determine the sleep stage or a sleep stage group that includes more than one sleep stage and is associated with a common therapy program. In other examples, sleep stage detection module 59 may compare a trend in the power level within a frequency band of the biosignal over time to a template in order to determine the sleep stage. In addition, in other examples, processor 50 may determine the sleep stage using another patient parameter alone or in addition to the biosignal from brain 13 (also referred to as a "bioelectrical brain signal"). For example, processor 50 may determine the sleep stage based on a bioelectrical brain signal and at least one of an electromyogram that indicates the electrical activity in a particular muscle or an electrooculogram, which indicates eye activity. Certain sleep stages may be associated with more muscle activity, more eye activity, or both.

After determining a sleep stage of patient 12 (92), processor 50 controls therapy delivery to one or more of the GPe, the STN, or the GPi, based on the determined sleep stage (94). In some examples, processor 50 controls therapy delivery to the one or more of the GPe, the STN, or the GPi by selecting one or more therapy programs from memory 52 (FIG. 3) based on the determined sleep stage. In other examples, processor 50 may control therapy delivery by modifying a therapy program stored in memory 52 of IMD 16 (FIG. 2) based on the determined sleep stage.

Processor 50 may activate electrical stimulation, deactivate electrical stimulation, increase an intensity of electrical stimulation, or decrease an intensity of electrical stimulation delivered to GPe, the STN, or the GPi based on the determined sleep stage. For example, processor 50 may independently select a particular therapy program to be delivered to GPe and a different therapy program to be delivered to at least one of the STN or the GPi based on the determined sleep stage. The therapy signals generated in accordance with the therapy programs may be delivered simultaneously or at different times (e.g., alternatively).

In some examples, processor 50 may control delivery of electrical stimulation to the STN and the GPi as shown in Table 4.

TABLE 4

Delivery of DBS based on determined sleep stage.

| Stage 1 | Deliver stimulation |
| REM | Deliver stimulation |
| Stage 2 | Deliver minimal to no stimulation |
| Deep Sleep | Deliver minimal to no stimulation |

For example, patient 12 may undergo more motor activity during the Stage 1 and REM sleep stages than during the Stage 2 and Deep Sleep sleep stages. Accordingly, processor 50 may adjust and deliver electrical stimulation to at least one of the STN or the GPi of brain 13 during the Stage 1 and REM sleep stages to help improve the motor function of patient 12, which may improve patient sleep quality. In some examples, stimulation generator 54 does not generate and deliver electrical stimulation to the at least one of the STN or the GPi of brain 13 during the other sleep stages, such as during the Stage 2 and/or Deep Sleep sleep stages. However, in some examples, stimulation generator 54 delivers a lower intensity of electrical stimulation (e.g., as indicated by a lower amplitude, frequency or shorter pulse width) to the at least one of the STN or the GPi during the Stage 2 and/or Deep Sleep sleep stages relative to the intensity of electrical stimulation delivered during the Stage 1 and REM sleep stages or relative to a respective threshold value.

Therefore, if sleep stage detection module 59 determines that patient 12 is in either the Stage 1 or REM sleep stages, then processor 50 may control stimulation generator 54 to activate or increase an intensity of electrical stimulation delivered to the at least one of the STN or the GPi based on the sleep stage indication generated by sleep stage detection module 59. The intensity of electrical stimulation delivered to the at least one of the STN or the GPi may be increased relative to a previously set value (e.g., a stimulation parameter value for a previously determined sleep stage) or relative to a baseline intensity level (e.g., as indicated by a particular stimulation threshold). In some examples, memory 52 of IMD 16 stores the baseline intensity level, which can be a minimum stimulation intensity level that is delivered to brain 13 of patient 12 regardless of a detected sleep state in order to maintain a particular patient state, such as a baseline state in which the patient symptoms are manageable. Despite the patient symptoms being manageable, further therapy delivery can be desirable in order to improve the patient state relative to the baseline state.

Additionally or alternatively, processor 50 may also decrease an intensity of the electrical stimulation delivered to the at least one of the STN or the GPi if patient 12 is in either the Stage 1 or REM sleep stages, depending upon the previous electrical stimulation settings. For example, if patient 12 has just entered the Stage 1 sleep stage for the first time during a sleep state, processor 50 may not necessarily decrease an intensity of electrical stimulation delivered to the at least one of the STN or the GPi because no previous delivery of electrical stimulation may have occurred. However, because patient 12 may cycle through the sleep stages, patient 12 may be in a sleep stage other than Stage 1 prior to re-entering the Stage 1 sleep stage. Thus, in some cases, processor 50 may decrease an intensity of electrical stimulation delivered to the at least one of the STN or the GPi of patient 12 in response to determining that patient 12 is in the Stage 1 sleep stage, e.g., if the therapy delivered during the previously detected sleep state had a higher intensity than that desired for the Stage 1 sleep stage.

Processor 50 may activate, increase an intensity, or decrease an intensity of electrical stimulation by selecting therapy programs and/or modifying electrical stimulation parameters of one or more currently selected therapy programs, or may deliver electrical stimulation according to one or more therapy programs selected from memory 52 based on a determination that patient 12 is in one of the Stage 1 or REM sleep stages. In some examples, in order to maintain a minimum level of stimulation intensity during the Stage 1 and/or REM sleep stages, processor 50 controls stimulation generator 54 to deliver stimulation therapy having a stimulation parameter value (e.g., a voltage or current amplitude, a frequency or a pulse width) greater than a threshold value to the at least one of the STN or the GPi of brain 13 during the Stage 1 and/or REM sleep stages. In addition, processor 50 can control stimulation generator 54 to deliver stimulation therapy having a stimulation parameter value (e.g., a voltage or current amplitude, a frequency or a pulse width)

greater than a threshold value to the at least one of the STN or the GPi of brain 13 during the Stage 1 and/or REM sleep stages.

In some examples, processor 50 may selectively control delivery of electrical stimulation by stimulation generator 54 to the at least one of the STN or the GPi of brain 13 during the Stage 2 and Deep Sleep sleep stages. During the Stage 2 and Deep Sleep stages, muscular activity of patient 12 may decrease and conscious awareness of the external environment may disappear. In some cases, during the Stage 2 sleep stage, patient 12 may continue to require delivery of electrical stimulation to the GPe in order to maintain the sleep state. Thus, in some examples, processor 50 continues to control stimulation generator 54 to deliver electrical stimulation to the GPe.

During the Stage 2 sleep stage, patient 12 may also exhibit relatively less motor activity than during the Stage 1 or REM sleep stages but relatively more motor activity than during the Deep Sleep sleep stage. Consequently, in some cases, patient 12 may continue to require delivery and adjustment of electrical stimulation to the at least one of the STN or the GPi during the Stage 2 sleep stage in order to control the symptoms of the sleep disorder associated with movement. In some examples, if sleep stage detection module 59 determines that patient 12 is in a Stage 2 sleep stage, then processor 50 may control electrical stimulator 54 to deliver electrical stimulation to GPe in order to maintain the sleep stage.

In addition, in some cases, as shown in Table 3 above, if sleep stage detection module 59 determines that patient 12 is in a Stage 2 sleep stage, then processor 50 may control stimulation generator 54 to deliver stimulation therapy to the at least one of the STN or the GPi of brain 13 during the Stage 2 sleep stage in order to control the symptoms of the sleep disorder associated with movement during the Stage 2 sleep stage. For example, processor 50 may activate, increase or decrease an intensity of electrical stimulation delivered to the at least one of the STN or the GPi during the Stage 2 sleep stage. In some examples, processor 50 controls stimulation generator 54 to deliver stimulation therapy having a stimulation parameter value (e.g., a voltage or current amplitude, a frequency or a pulse width) greater than a threshold value to the at least one of the STN or the GPi of brain 13 during the Stage 2 sleep stage.

However, in some cases, the Stage 2 sleep stage of patient 12 may naturally require almost no movement and patient 12 may not consciously move as much as in other sleep stages. For example, patient 12 may not experience involuntary movements or at least experience minimal involuntary movements. Thus, patient 12 may not require stimulation of the at least one of the STN or the GPi during the Stage 2 sleep stage. Thus, in some examples, processor 50 may activate, deactivate or decrease an intensity of electrical stimulation delivered to the at least one of the STN or the GPi during the Stage 2 sleep stage based on the sleep stage indication generated by sleep stage detection module 59. In some examples, the processor 50 controls stimulation generator 54 to deliver stimulation therapy having a stimulation parameter value (e.g., a voltage or current amplitude, a frequency or a pulse width) less than a threshold value to the at least one of the STN or the GPi of brain 13 during the Stage 2 sleep stage.

During the Deep Sleep sleep stage, patient 12 may require little to no delivery of electrical stimulation to the at least one of the STN or the GPi compared to the parameters delivered during the Stage 1, Stage 2, or REM sleep stages. If patient 12 is in the Deep Sleep sleep stage, then processor 50 may deactivate or decrease the intensity of electrical stimulation delivered to the at least one of the STN or the GPi relative to the intensity of electrical stimulation delivered during the Stage 1, Stage 2, or REM sleep stages based on the Deep Sleep sleep stage indication generated by sleep stage detection module 59. In some examples, processor 50 controls stimulation generator 54 to deliver stimulation therapy having a stimulation parameter value (e.g., a voltage or current amplitude, a frequency or a pulse width) lower than a second threshold value to the at least one of the STN or the GPi of brain 13 during the Deep Sleep sleep stage. The threshold value may be different from that used to control the stimulation therapy to the at least one of the STN or the GPi during the Stage 2 sleep stage and may be lower than that used to control stimulation therapy to the at least one of the STN or the GPi during the Stage 1 and REM sleep stages.

Processor 50 may also determine whether the sleep state has ended (96) in order to, for example, revert to a different therapy program or revert to a different technique for controlling delivery of electrical stimulation by IMD 16 when patient 12 is awake. In some examples, processor 50 may use techniques similar to those described above with respect to detecting the sleep state in order to determine whether the sleep state has ended. For example, patient 12 may provide input to programmer 14 indicating that the present patient state is an awake state and processor 70 of programmer 14 may transmit a signal to processor 50 to indicate that the sleep state has ended. In other examples, processor 50 may determine patient 12 is in an awake state based on the monitored biosignal and/or monitored physiological parameter values, such as a patient posture or activity level, as well as other physiological parameters.

If the sleep state has ended, then processor 50 may stop detecting the patient sleep stage until the sleep state is detected again (86). If the sleep state has not ended, then processor 50 may continue to monitor the biosignal from brain 13 (88) and continue to determine a sleep stage based on a frequency characteristic of the biosignal (90, 92) in order to control therapy (94).

In some cases, patient 12 may suffer from poor sleep quality, which may result in excessive sleepiness during the day. In some examples, IMD 16 is configured to deliver electrical stimulation therapy to the GPe during an awake state of patient 12, the electrical stimulation therapy being configured to help patient 12 stay awake and not fall asleep. The electrical stimulation parameter values differ from the electrical stimulation that are configured to help patient 12 fall asleep, and to maintain sleep or certain sleep stages. Electrical stimulation of the GPe configured to help patient 12 stay awake may be useful when patient 12 is engaged in certain tasks, such as driving. The electrical stimulation may be delivered to the GPe during the awake state of the patient 12 alone or in combination with another therapy, such as, but not limited to, electrical stimulation therapy to at least one of the STN or the GPi, configured to help improve motor function of patient 12.

FIG. 7 is a flow diagram of an example technique for controlling therapy delivery to the GPe of brain 13 of patient 12 during an awake state of patient 12. In accordance with the technique shown in FIG. 7, processor 50 determines whether patient 12 is in an awake state (100). In some examples, processor 50 may use techniques similar to those described above with respect to detecting the sleep state (e.g., described with respect to block 80 of FIG. 5) in order to determine whether patient 12 is in an awake state. For example, patient 12 may provide input to IMD 16 or to programmer 14 indicating the present patient state is an awake state. If the input is provided to programmer 14, processor 70 of programmer 14 may transmit a signal to processor 50 to indicate that patient 12 is currently in the awake state. In other examples, processor 50 may determine patient 12 is in an awake state based on the monitored biosignal and/or monitored physiological parameter values, such as a patient posture or activity level, as well as the other physiological parameters described above.

In response to determining patient 12 is in an awake state ("YES" branch of block 100), processor 50 controls stimulation generator 54 to deliver electrical stimulation to the GPe (104). The electrical stimulation delivered to the GPe may be configured to help patient 12 stay awake and, therefore, help prevent patient 12 from falling asleep. In some examples, processor 50 controls stimulation generator 54 to deliver electrical stimulation to the GPe substantially continuously (e.g., continuously or nearly continuously) during the awake state. In other examples, processor 50 controls stimulation generator 54 to deliver electrical stimulation to the GPe periodically during the awake state. For example, processor 50 may control stimulation generator 54 to deliver electrical stimulation to the GPe according to a predetermined schedule or cycle. As another example, processor 50 may control stimulation generator 54 to deliver electrical stimulation to the GPe in response to determining patient 12 is engaged in certain activities (e.g., driving). Processor 50 may determine patient 12 is engaged in the certain activities based on, for example, user input received via IMD 16 or programmer 14, based on one or more patient parameters, such as those described above with respect to determining whether patient 12 is in a sleep state, or any combination thereof.

Processor 50 controls stimulation generator 54 to deliver electrical stimulation to the GPe (104) until processor 50 determines that patient 12 is not in the awake state. As shown in FIG. 7, in response to determining patient 12 is not in an awake state, e.g., is in a sleep state ("NO" branch of block 100), processor 50 controls stimulation generator 54 to withhold the delivery of electrical stimulation to the GPe that is configured to help patient 12 stay awake (102). Processor 50 may determine patient 12 is not in an awake state by, for example, determining patient 12 is in a sleep state, e.g., using the techniques described with respect to FIGS. 5 and 6. In some examples, processor 50 may control stimulation generator 54 to withhold all delivery of electrical stimulation to the GPe in response to determining patient 12 is not in the awake state. In other examples, processor 50 control stimulation generator 54 to deliver other electrical stimulation to the GPe in response to determining patient 12 is not in the awake state, such as electrical stimulation described with respect to FIG. 7, which is configured to help patient 12 fall asleep, maintain sleep or certain sleep stages, achieve a higher quality of sleep, or any combination thereof.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, electrical stimulation devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
   determining, by a processor, a patient is in a sleep state; and
   controlling, by the processor, an electrical stimulation generator to deliver deep brain electrical stimulation to a globus pallidus externus of a brain of the patient according to a therapy program defining electrical stimulation configured to induce sleep of the patient, based on the determination that the patient is in the sleep state.

2. The method of claim 1, wherein controlling the electrical stimulation generator to deliver electrical stimulation to the globus pallidus externus comprises controlling the electrical stimulation generator to initiate delivery of electrical stimulation to the globus pallidus externus according to the therapy program in response to detecting the sleep state.

3. The method of claim 1, wherein determining the patient is in the sleep state comprises receiving user input indicating the sleep state.

4. The method of claim 1, wherein determining the patient is in the sleep state comprises:
   receiving, by the processor, a signal indicative of a patient parameter of the patient; and
   determining whether the patient is in the sleep state based on the signal indicative of the patient parameter.

5. The method of claim 4, wherein the patient parameter comprises at least one of an activity level, a patient posture, a heart rate, a respiration rate, a respiratory volume, a blood pressure, a blood oxygen saturation, a partial pressure of oxygen within blood, a partial pressure of oxygen within cerebrospinal fluid, muscular activity, a core temperature, an arterial blood flow or a galvanic skin response of the patient.

6. The method of claim 1, wherein determining the patient is in the sleep state comprises:
determining an activity level of the patient; and
determining whether the patient is in the sleep state based on the activity level of the patient.

7. The method of claim 1, further comprising:
determining, by the processor, the patient is in an awake state; and
controlling the electrical stimulation generator to deactivate delivery of electrical stimulation to the globus pallidus externus according to the therapy program in response to determining the patient is in the awake state.

8. The method of claim 7, wherein determining the patient is in the awake state comprises receiving user input indicating the awake state.

9. The method of claim 7, wherein determining the patient is in the awake state comprises:
receiving, by the processor, a signal indicative of a physiological parameter of the patient; and
determining whether the patient is in the awake state based on the signal indicative of the physiological parameter.

10. The method of claim 7, wherein determining the patient is in the awake state comprises:
determining an activity level of the patient; and
determining whether the patient is in the awake state based on the activity level of the patient.

11. The method of claim 1, wherein controlling the electrical stimulation generator to deliver electrical stimulation to the globus pallidus externus comprises controlling the electrical stimulation generator to deliver electrical stimulation to the globus pallidus externus according to the therapy program substantially continuously during the sleep state.

12. The method of claim 1, further comprising determining a sleep stage of the patient, wherein controlling the electrical stimulation generator to deliver electrical stimulation to the globus pallidus externus comprises controlling the electrical stimulation generator to deliver electrical stimulation to the globus pallidus externus according to the therapy program based on the determined sleep stage of the patient.

13. The method of claim 12, wherein determining the sleep stage of a patient comprises:
receiving, from a sensing module, a biosignal that is indicative of activity within the brain of the patient; and
determining the sleep stage based on the biosignal.

14. The method of claim 12, wherein determining the sleep stage of a patient comprises determining whether the patient is in at least one of: a Stage 1 sleep stage, a rapid eye movement sleep stage, a Deep Sleep sleep stage, or a Stage 2 sleep stage.

15. The method of claim 1, wherein the therapy program comprises a first therapy program, the method further comprising controlling, by the processor, the electrical stimulation generator to deliver electrical stimulation to at least one of a subthalamic nucleus or a globus pallidus internus of the brain of the patient according to a second therapy program based on the determination that the patient is in the sleep state, wherein delivery of electrical stimulation to the globus pallidus externus according to the first therapy program and delivery of the electrical stimulation to the at least one of the subthalamic nucleus or the globus pallidus internus according to the second therapy program are independently controlled.

16. The method of claim 15, further comprising determining a sleep stage of the patient, wherein controlling the electrical stimulation generator to deliver electrical stimulation to the at least one of the subthalamic nucleus or the globus pallidus internus of the brain of the patient according to the second therapy program comprises controlling the electrical stimulation generator to deliver electrical stimulation to the at least one of the subthalamic nucleus or the globus pallidus internus according to the second therapy program based on the determined sleep stage of the patient.

17. The method of claim 16, wherein controlling the electrical stimulation generator to deliver electrical stimulation to the globus pallidus externus according to the first therapy program and the at least one of the subthalamic nucleus or the globus pallidus internus according to the second therapy program comprises controlling the electrical stimulation generator to deliver electrical stimulation according to the first and second therapy programs substantially simultaneously.

18. The method of claim 16, wherein controlling the electrical stimulation generator to deliver electrical stimulation to the globus pallidus externus according to the first therapy program and the at least one of the subthalamic nucleus or the globus pallidus internus according to the second therapy program comprises controlling the electrical stimulation generator to deliver electrical stimulation according to the first and second therapy programs at different times.

19. The method of claim 16, wherein controlling the electrical stimulation generator to deliver electrical stimulation according to at least one of the first or second therapy programs comprises modifying at least one therapy parameter value of at least one of the first or second therapy programs based on the determined sleep stage.

20. The method of claim 15, wherein the second therapy program is different than the first therapy program, the second therapy program defining electrical stimulation configured to manage a symptom of a movement disorder of the patient.

21. The method of claim 1, wherein the sleep state is at least one of: a first state in which the patient is awake and intending on sleeping, a second state in which the patient is awake and is attempting to sleep, or a third state in which the patient is asleep.

22. A system comprising:
an electrical stimulation generator; and
a processor configured to determine a patient is in a sleep state and control the electrical stimulation generator to deliver deep brain electrical stimulation to a globus pallidus externus of a brain of the patient according to a therapy program defining electrical stimulation configured to induce sleep of the patient, based on the determination that the patient is in the sleep state.

23. The system of claim 22, wherein the processor is configured to control the electrical stimulation generator to deliver electrical stimulation to the globus pallidus externus by at least controlling, in response to detecting the sleep state, the electrical stimulation generator to initiate delivery of electrical stimulation to the globus pallidus externus according to the therapy program.

24. The system of claim 22, further comprising a user interface, wherein the processor is configured to determine the patient is in the sleep state by at least receiving user input indicating the sleep state via the user interface.

25. The system of claim 22, further comprising a sensor configured to generate a signal indicative of a patient parameter of the patient, wherein the processor is configured to determine the patient is in the sleep state by at least determining whether the patient is in the sleep state based on the signal indicative of the patient parameter.

26. The system of claim 25, wherein the patient parameter comprises at least one of an activity level, a patient posture, a heart rate, a respiration rate, a respiratory volume, a blood pressure, a blood oxygen saturation, a partial pressure of oxygen within blood, a partial pressure of oxygen within cerebrospinal fluid, muscular activity, a core temperature, an arterial blood flow or a galvanic skin response of the patient.

27. The system of claim 22, wherein the processor is configured to determine the patient is in the sleep state by at least:
    determining an activity level of the patient; and
    determining whether the patient is in the sleep state based on the activity level of the patient.

28. The system of claim 22, wherein the processor is further configured to determine the patient is in an awake state, and control the electrical stimulation generator to deactivate delivery of electrical stimulation to the globus pallidus externus according to the therapy program in response to determining the patient is in the awake state.

29. The system of claim 28, further comprising a user interface, wherein the processor is configured to determine the patient is in the awake state by at least receiving user input indicating the awake state.

30. The system of claim 28, further comprising a sensor configured to generate a signal indicative of a patient parameter of the patient, wherein the processor is configured to determine the patient is in the awake state by at least determining whether the patient is in the awake state based on the signal indicative of the patient parameter.

31. The system of claim 28, wherein the processor is configured to determine the patient is in the awake state by at least:
    determining an activity level of the patient; and
    determining whether the patient is in the awake state based on the activity level of the patient.

32. The system of claim 22, wherein the processor is configured to control the electrical stimulation generator to deliver electrical stimulation to the globus pallidus externus by at least controlling the electrical stimulation generator to deliver electrical stimulation to the globus pallidus externus according to the therapy program substantially continuously during the sleep state.

33. The system of claim 22, wherein the processor is further configured to determine a sleep stage of the patient, and wherein the processor is configured to control the electrical stimulation generator to deliver electrical stimulation to the globus pallidus externus by at least controlling the electrical stimulation generator to deliver electrical stimulation to the globus pallidus externus according to the therapy program based on the determined sleep stage of the patient.

34. The system of claim 33, further comprising a sensing module configured to sense a biosignal that is indicative of activity within the brain of the patient, wherein the processor is configured to determine the sleep stage of a patient based on the biosignal.

35. The system of claim 33, wherein the processor is configured determine the sleep stage of the patient by at least determining whether the patient is in at least one of Stage 1, rapid eye movement, Deep Sleep, or Stage 2 sleep stages.

36. The system of claim 22, wherein the therapy program comprises a first therapy program, and wherein the processor is configured to control the electrical stimulation generator to deliver electrical stimulation to at least one of a subthalamic nucleus or a globus pallidus internus of the brain of the patient according to a second therapy program based on the determination that the patient is in the sleep state, wherein the processor is configured to independently control the delivery of electrical stimulation to the globus pallidus externus according to the first therapy program and the delivery of the electrical stimulation to the at least one of the subthalamic nucleus or the globus pallidus internus according to the second therapy program.

37. The system of claim 36, wherein the processor is further configured determine a sleep stage of the patient, and control the electrical stimulation generator to deliver electrical stimulation to the at least one of the subthalamic nucleus or the globus pallidus internus according to the second therapy program of the brain of the patient based on the determined sleep stage of the patient.

38. The system of claim 36, wherein the second therapy program is different than the first therapy program, the second therapy program defining electrical stimulation configured to manage a symptom of a movement disorder of the patient.

39. The system of claim 36, wherein the processor is configured to control the electrical stimulation generator to deliver electrical stimulation to the globus pallidus externus according to the first therapy program and the at least one of the subthalamic nucleus or the globus pallidus internus according to the second therapy program substantially simultaneously.

40. The system of claim 36, wherein the processor is configured to control the electrical stimulation generator to deliver electrical stimulation to the globus pallidus externus according to the first therapy program and the at least one of the subthalamic nucleus or the globus pallidus internus according to the second therapy program at different times.

41. The system of claim 36, wherein the processor is configured to control the electrical stimulation generator to deliver electrical stimulation according to at least one of the first or second therapy programs by at least modifying at least one therapy parameter value of at least one of the first or second therapy programs based on the determined sleep stage.

42. The system of claim 22, wherein the sleep state is at least one of: a first state in which the patient is awake and intending on sleeping, a second state in which the patient is awake and is attempting to sleep, or a third state in which the patient is asleep.

43. A system comprising:
    means for generating electrical stimulation;
    means for determining a patient is in a sleep state; and
    means for controlling the means for generating electrical stimulation to deliver deep brain electrical stimulation to a globus pallidus externus of a brain of the patient according to a therapy program defining electrical stimulation configured to induce sleep of the patient, based on a determination, by the means for determining, that the patient is in the sleep state.

44. The system of claim 43, wherein the means for controlling controls the means for generating electrical stimulation to initiate delivery of electrical stimulation to the globus pallidus externus according to the therapy program in response to detecting the sleep state.

45. The system of claim 43, wherein the sleep state is at least one of a first state in which the patient is awake and intending on sleeping, a second state in which the patient is awake and is attempting to sleep, or a third state in which the patient is asleep.

46. A non-transitory computer-readable medium comprising instructions that, when executed by a processor, cause the processor to:
  determine a patient is in a sleep state; and
  in response to determining the patient is in the sleep state, control an electrical stimulation generator to deliver deep brain electrical stimulation to a globus pallidus externus of a brain of the patient according to a therapy program defining electrical stimulation configured to induce sleep of the patient, based on the determination that the patient is in the sleep state.

47. The non-transitory computer-readable medium of claim 46, wherein the instructions cause the processor to control the electrical stimulation generator to initiate delivery of electrical stimulation to the globus pallidus externus according to the therapy program in response to detecting the sleep state.

48. The non-transitory computer-readable medium of claim 46, wherein the sleep state is at least one of: a first state in which the patient is awake and intending on sleeping, a second state in which the patient is awake and is attempting to sleep, or a third state in which the patient is asleep.

* * * * *